United States Patent
Gannoe et al.

(10) Patent No.: US 6,994,669 B1
(45) Date of Patent: Feb. 7, 2006

(54) APPARATUS AND METHOD FOR CARDIAC SURGERY

(75) Inventors: James R. Gannoe, Redwood City, CA (US); Daniel M. Brounstein, San Mateo, CA (US); Meir Moshe, El Sobrante, CA (US); Jan Komtebedde, Los Gatos, CA (US); David Evans, Fishers, IN (US); Andrew H. Hancock, Fremont, CA (US)

(73) Assignee: Heartport, Inc., Redwood City, CA (US)

( * ) Notice: Subject to any disclaimer, the term of this patent is extended or adjusted under 35 U.S.C. 154(b) by 0 days.

(21) Appl. No.: 09/492,558

(22) Filed: Jan. 27, 2000

Related U.S. Application Data

(63) Continuation-in-part of application No. 09/293,630, filed on Apr. 15, 1999.

(51) Int. Cl.
*A61B 1/32* (2006.01)

(52) U.S. Cl. .................................... 600/232

(58) Field of Classification Search ............. 600/210, 600/213, 232, 231, 201, 235, 222, 228, 229, 600/215, 209
See application file for complete search history.

(56) References Cited

U.S. PATENT DOCUMENTS

| | | | |
|---|---|---|---|
| 4,048,990 A | 9/1977 | Goetz | |
| 4,350,160 A | 9/1982 | Kolesov et al. | |
| 5,108,412 A | 4/1992 | Krumeich et al. | |
| 5,119,804 A | 6/1992 | Anstadt | |
| 5,131,905 A | 7/1992 | Grooters | |
| RE34,150 E | 12/1992 | Santilli et al. | |
| 5,437,651 A | 8/1995 | Todd et al. | |
| 5,447,149 A | 9/1995 | Kikawada et al. | |
| 5,484,391 A | 1/1996 | Buckman, Jr. et al. | |
| 5,509,890 A | 4/1996 | Kazama | |
| 5,571,074 A | 11/1996 | Buckman, Jr. et al. | |
| 5,582,580 A | 12/1996 | Buckman, Jr. et al. | |
| 5,836,311 A * | 11/1998 | Borst et al. ................. | 128/897 |
| 5,906,607 A | 5/1999 | Taylor et al. | |
| 5,976,080 A * | 11/1999 | Farascioni .................. | 600/213 |
| 6,015,378 A | 1/2000 | Borst et al. | |
| 6,071,235 A * | 6/2000 | Furnish et al. .............. | 600/201 |
| 6,102,854 A * | 8/2000 | Cartier et al. ............... | 600/228 |
| 6,113,534 A * | 9/2000 | Koros et al. ................ | 600/213 |

(Continued)

FOREIGN PATENT DOCUMENTS

| | | |
|---|---|---|
| GB | 2 140 695 A | 12/1984 |

(Continued)

OTHER PUBLICATIONS

Kolessov V.I., The Surgery of Coronary Arteries of the Heart, Leningrad, Meditsina, 1977, pp 360 (Russian Article).

(Continued)

*Primary Examiner*—Pedro Philogene
(74) *Attorney, Agent, or Firm*—Brian Tomko

(57) ABSTRACT

The invention provides a stabilizer having a foot to stabilize a patient's heart. The stabilizer has a first foot which is larger than a second foot. The first foot has lateral surfaces which are used to retract other parts of the heart while contact surfaces stabilize the target artery.

13 Claims, 32 Drawing Sheets

U.S. PATENT DOCUMENTS

| | | | |
|---|---|---|---|
| 6,132,370 A * | 10/2000 | Furnish et al. | 600/215 |
| 6,152,874 A * | 11/2000 | Looney et al. | 600/222 |
| 6,210,323 B1 * | 4/2001 | Gilhuly et al. | 600/208 |
| 6,213,940 B1 * | 4/2001 | Sherts et al. | 600/231 |
| 6,213,941 B1 * | 4/2001 | Benetti et al. | 600/235 |
| 6,231,506 B1 * | 5/2001 | Hu et al. | 600/210 |
| 6,231,585 B1 | 5/2001 | Takahashi et al. | |
| 6,251,065 B1 | 6/2001 | Kochamba et al. | |
| 6,254,532 B1 | 7/2001 | Paolitto et al. | |
| 6,254,535 B1 | 7/2001 | Furnish et al. | |
| 6,338,710 B1 | 1/2002 | Takahashi et al. | |
| 6,379,297 B1 | 4/2002 | Furnish et al. | |
| 6,656,113 B2 * | 12/2003 | Green, II et al. | 600/235 |

FOREIGN PATENT DOCUMENTS

| | | |
|---|---|---|
| WO | WO 94/0312 | 2/1994 |
| WO | WO 99/16367 A1 | 4/1999 |
| WO | WO 00/15119 | 3/2000 |

OTHER PUBLICATIONS

Kolessov V.I., The Surgery of Coronary Arteries of the Heart, Leningrad, Meditsina, 1977, pp 360 (English Translation).

Anstadt et al., "Direct Mechanical Ventricular Actuation for Cardiac Arrest in Humans, A Clinical Feasibility Trial", The Cardiopulmonary Journal, vol. 100, Jul.-Dec., 1991, pp. 86-92.

DelRossi, A.J., et al., "A New Retractor to Aid in Coronary Artery Surgery", Annals of Thoracic Surgery, vol. 36, No. 1, Jul. 1983, pp101-102.

Conolly, John E., "Assisted Circulation" The Textbook of Surgery, the Biological Basis of Modern Surgical Practice, 10th edition, 1972, pp. 2114-2023.

Supplementary European Search Report EP01903397 dated Aug. 9, 2004.

* cited by examiner

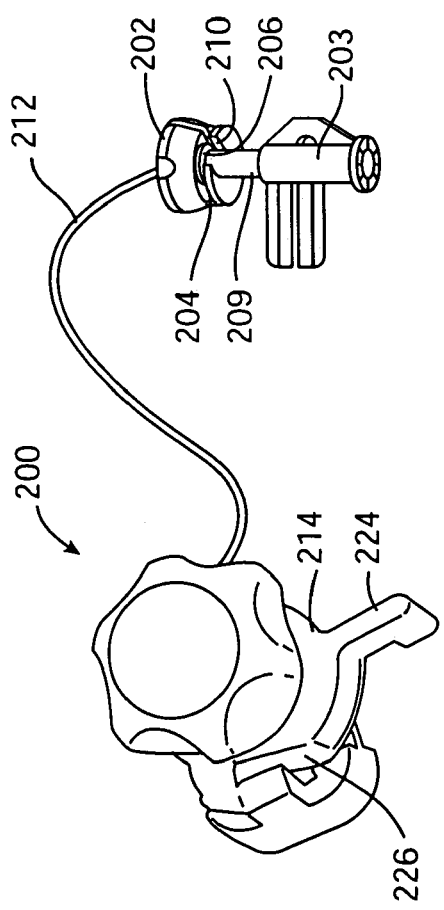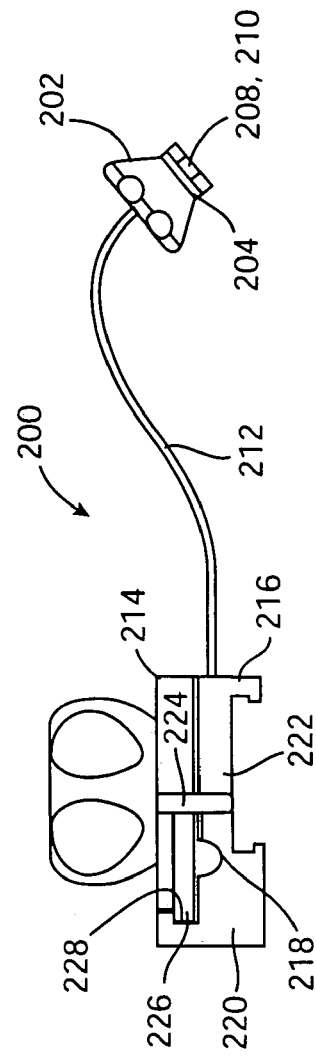
FIG. 15A
FIG. 15B

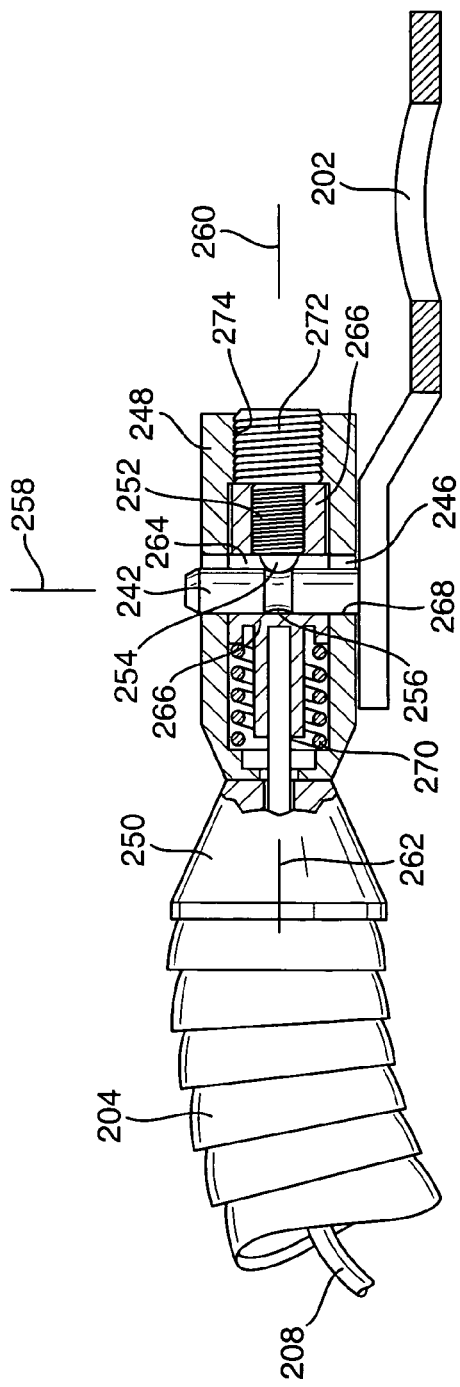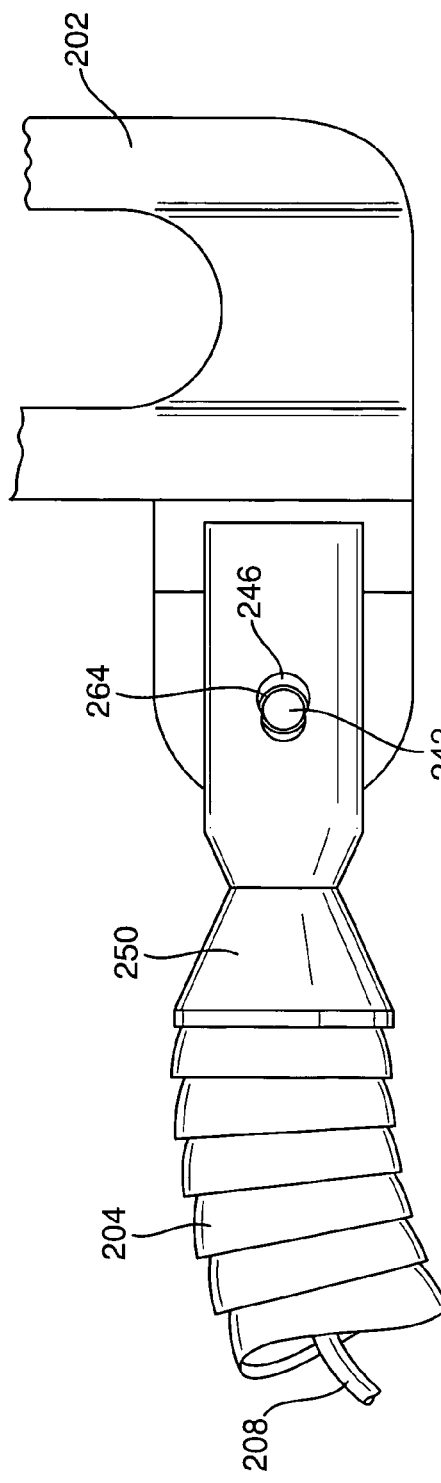
FIG. 26
FIG. 25

APPARATUS AND METHOD FOR CARDIAC SURGERY

CROSS-REFERENCE TO RELATED APPLICATIONS

This application is a continuation-in-part of, and claims the benefit of priority from U.S. patent application Ser. No. 09/293,630, filed Apr. 15, 1999, the full disclosure of which is incorporated herein by reference.

FIELD OF THE INVENTION

The present invention relates generally to surgical instruments, and more specifically to retractors and instruments for performing heart surgery.

BACKGROUND OF THE INVENTION

In conventional heart surgery, an incision is made in the chest, either through the sternum (a median sternotomy) or between the ribs (a thoracotomy) in order to gain access into the chest cavity. A retractor is placed in the chest incision which allows the chest bones and tissue to be spread apart to create a wide opening. Surgical instruments are then placed through this opening to perform surgery on the heart.

One of the most common types of heart surgery is coronary artery bypass grafting, or CABG. In CABG, a blockage in one or more coronary arteries is bypassed by connecting a graft vessel to the coronary artery downstream of the blockage. The technique of connecting the graft vessel to the coronary artery is known as anastomosis. The graft vessel may be a mammary artery dissected from the chest wall, wherein the upstream end of the artery is left intact and the downstream end is attached to the coronary artery. Alternatively, the graft vessel may be a section of artery or vein from elsewhere in the patient's body, or an artificial vascular graft, wherein the upstream end of the graft is attached to an artery such as the aorta, and the downstream end is connected to the coronary artery. In this way, multiple coronary artery blockages at various locations on the front, side or back of the heart may be bypassed using multiple graft vessels.

Conventionally, CABG is performed with the heart stopped, while the patient is supported on cardiopulmonary bypass, whereby the patient's blood is circulated by means of an extracorporeal pump and oxygenation system. In certain cases, however, CABG may be performed with the heart beating in a technique known as "beating heart" or "off-pump" coronary artery bypass (OPCAB), allowing cardiopulmonary bypass to be avoided. In OPCAB, the surface of the heart near the anastomosis site on the coronary artery is stabilized using a specialized instrument while the heart continues to beat. This local stabilization keeps the anastomosis site as motionless as possible while the graft vessel is connected to the coronary artery. The coronary artery is temporarily occluded or a temporary shunt is inserted into the coronary artery during the anastomosis to keep the site free of blood.

The basic functions required in an OPCAB procedure include sternal or rib retraction, heart manipulation, heart stabilization, pericardial retraction, coronary traction and hemostasis. Sternal retraction involves prying apart the opposing halves of the divided sternum to open the chest cavity. Heart manipulation entails moving, turning or lifting the heart in order to access coronary arteries on the front, back or sides of the heart. Heart stabilization is the process of stabilizing the surface of the beating heart near the anastomosis site to allow the anastomosis to be performed. Pericardial retraction is used to pull the incised pericardium out of the way for better access to the heart. Coronary retraction involves placing a suture or silastic under the coronary arteries near the anastomosis site and exerting traction on the suture or silastic so as to better expose the coronary artery. This traction may also serve to occlude the coronary artery above and below the anastomosis site to provide hemostasis. In some cases, a temporary shunt may be inserted through an arteriotomy in the coronary artery to allow blood to flow past the anastomosis site during the procedure.

SUMMARY OF THE INVENTION

The present invention provides systems for performing OPCAB and other types of cardiac surgery which overcome many of the drawbacks of current devices. The system provides additional degrees of freedom and ranges of position than currently available devices. The invention enables sternal or rib retraction, pericardial retraction, heart manipulation, coronary traction, and heart stabilization using a single integrated system. While providing such functionality, the systems of the invention preferably utilize an entirely reusable retraction platform, thereby eliminating the waste and cost associated with some current systems.

In a first embodiment, the invention provides an apparatus for performing surgery on a heart of a patient comprising a first arm, a second arm and an actuator, the actuator moving the first arm relative to the second arm. The apparatus further includes a first blade on the first arm and a second blade on the second arm, the first and second blades having first and second surfaces facing away from each other, the first and second surfaces being adapted to atraumatically engage tissue or bone for the retraction thereof. The apparatus also includes a stabilizer adapted to be mounted to one of the first and second arms and having a foot, the foot being configured to atraumatically engage the surface of the heart. In a preferred embodiment, the first and second blades are removably coupled to the first and second arms whereby the first and second blades may be removed and replaced with alternate blades. The ability to quickly and easily remove and replace blades allows the surgeon to select the ideal blade for the particular patient and procedure being performed. The apparatus of the invention thus allows blades of various size, shape, and material to be interchanged. Preferably, the arms and blades are a biocompatible metal so as to be resterilizable and reusable, but alternatively either or both could be made of plastic or other suitable material and could be individually packaged and sterilized for single use.

In a second embodiment, the apparatus of the invention has a receptacle on at least one of the first and second arms. A suture stay is removably mounted to the receptacle, thus allowing sutures for pericardial retraction or for other purposes to be positioned in the suture stay and retained therein during a procedure. Preferably, the suture stay is plastic or other disposable material, allowing the suture stay to be removed from the receptacle and discarded after use. Usually, the suture stay will accommodate a plurality of individual sutures, and/or the arms include a plurality of receptacles to accommodate multiple suture stays. In an exemplary embodiment, the receptacle comprises a cavity in the arm adapted to receive the suture stay. A retention mechanism is provided on the suture stay and/or on the arm to releasably retain the suture stay in the cavity.

The suture stay preferably comprises a body having an inner edge and an outer edge and retention structure on the body for retaining the body on a blade of the surgical retractor. At least one channel extends through the body from the inner edge to the outer edge and is adapted to removably receive a suture therein. Additionally, a clamp is coupled to the body adjacent to the channel and is adapted to releasably retain the suture in the channel. Usually, the suture stay will be placed in a bag, pouch or other container and sterilized separately from the arms and other components of the apparatus.

In a further embodiment, an apparatus for performing surgery on a heart of a patient comprises a rack, a first arm and a second arm mounted to the rack, the first arm being movable relative to the rack and relative to the second arm. A first blade is mounted to the first arm and a second blade is mounted to the second arm, the first and second blades having first and second surfaces facing away from each other, the first and second surfaces being adapted to atraumatically engage tissue or bone for the retraction thereof. A first rail is disposed on the first arm, a second rail is disposed on the second arm, and a third rail is disposed on the rack. The apparatus further includes a stabilizer adapted to be coupled to any one of the first rail, second rail or third rail, the stabilizer having a foot, the foot being configured to atraumatically engage the surface of the heart.

The invention further provides a stabilizing device for stabilizing a site on an outer surface of a patient's heart to facilitate surgery thereon. In one embodiment, the stabilizing device comprises a shaft, a foot coupled to the shaft having a contact surface for atraumatically engaging the outer surface of the heart, and a mount having a first coupling for attachment to a chest retractor, a second coupling for attachment to the shaft, a first movable joint interconnected between the first and second couplings, and a second movable joint interconnected between the first joint and the second coupling. Preferably, each of the first and second joints is movable about at least two axes of rotation. For example, the first and second joints may comprise spherical joints or ball-in-socket joints. In one embodiment, the first joint comprises a first hemispherical member centered on a first axis and the second joint comprises a second hemispherical member centered on a second axis, the first and second axes being non-parallel, and preferably being generally perpendicular.

In another aspect of the present invention, an apparatus for stabilizing an the surface of the heart has a shaft and a foot. The foot has a first arm, a second arm, Tand a space between the first and second arms. The first and second arms each having a contact surface for engaging the heart, a proximal end, a distal end and a length defined between the proximal and distal ends. The length of the first arm is preferably longer, more preferably at least 30% longer, than the length of the second arm.

In another aspect of the invention, the foot includes a bottom surface having a contact surface generally lying in a plane. Lateral surfaces taper away from the plane to provide retraction of adjacent structures.

In still another aspect of the present invention, the foot has a contact surface and a slot in which a vessel on the heart may be positioned. The slot is aligned with a central axis and the foot has a shape which is asymmetrical relative to the central axis. In yet another aspect of the present invention, the arm is attached to the arm at a location offset from the axis.

In a further aspect of the invention, a flexible arm for holding a medical instrument is provided. The arm has a plurality of links each having a hole therethrough. An elongate element extends through the holes so that tension on the elongate element locks the links in a fixed orientation. A frictional element, such as a wire screen, is positioned between adjacent links to enhance frictional engagement between adjacent links when the cable is tensioned. The frictional element may be applied, adhered or embedded on one side of the link to provide a relatively hard, textured surface opposing a softer surface of the link.

In still a further aspect of the present invention, arm has a base link which is rotatable relative to the body about an axis. The base link directs the elongate element at an angle relative to the axis and also is displaced from the pivoting axis by at least 0.3 inch and more preferably at least 0.5 inch. The base link preferably directs the elongate element at an angle of 45–90 degrees relative to the pivoting axis.

In still another aspect of the present invention, a device for stabilizing a medical device includes a base and an arm. The medical device is coupled to the distal end of the arm and pivots relative to the arm around an axis which is offset, preferably forming an angle of 70–110 degrees, relative to an axis defined by the arm.

In still a further aspect of the present invention, a suction element for stabilizing a patient's heart is provided. The suction element has a malleable skeleton and a coating over the skeleton. The malleable skeleton has hinges formed by thinner portions of the coating, and preferably by exposed portions of the skeleton, which permit the user to bend and distort the suction element.

A further understanding of the nature and advantages of the invention and further aspects and advantages of the invention may be realized by reference to the remaining portion of the specification and the drawings.

BRIEF DESCRIPTION OF THE DRAWINGS

FIGS. 15A–15B are perspective and side views, respectively, of a vascular clamp holder according to the invention.

FIG. 25 shows a foot attached to the distal end of the arm.

FIG. 26 is a cross-sectional view of the distal end of the arm.

DETAILED DESCRIPTION OF THE SPECIFIC EMBODIMENTS

Figure 1:
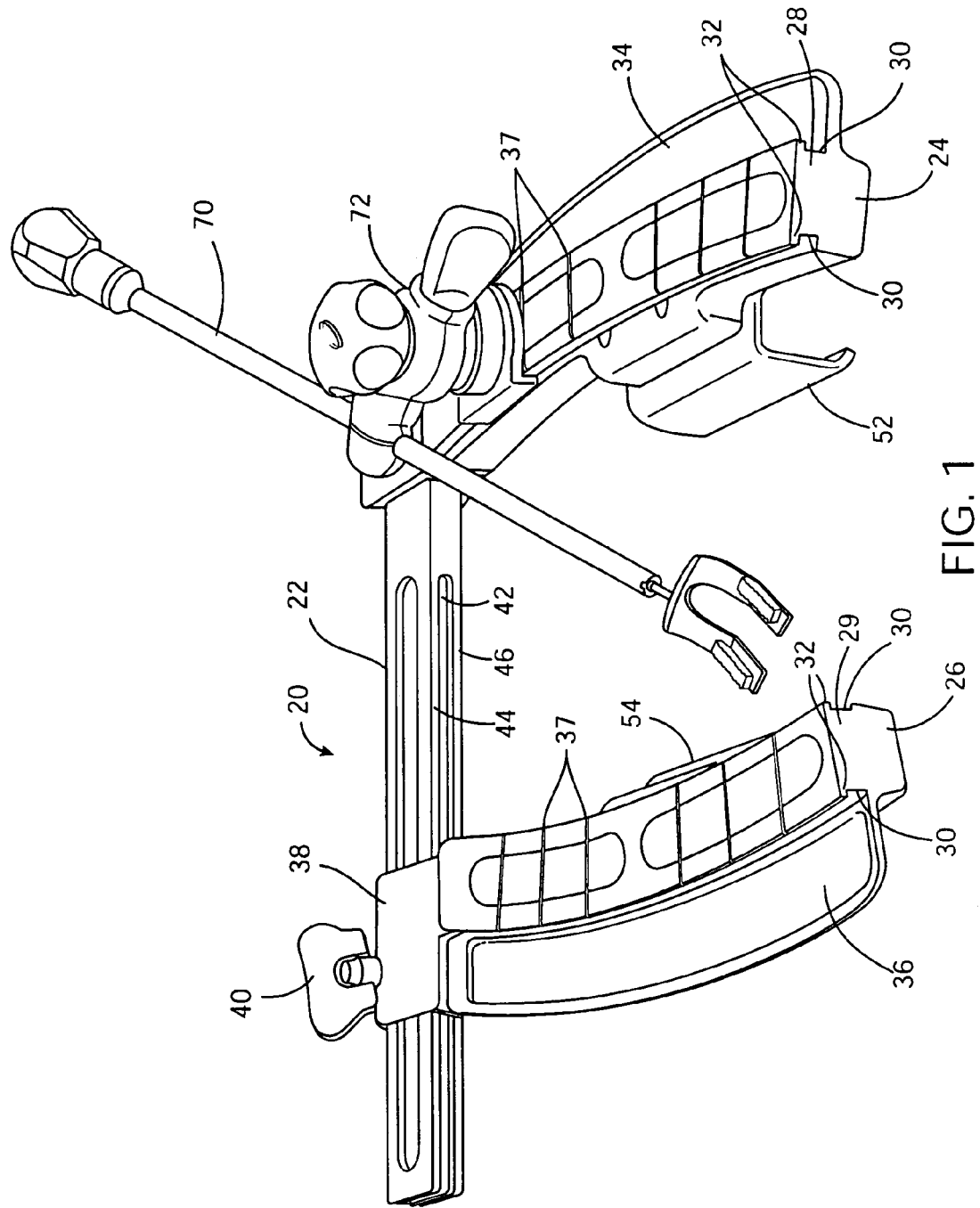
FIG. 1 is a perspective view of a retraction and stabilization system according to the invention.

A system for performing cardiac surgery according to the invention includes a retractor for retraction of a sternotomy or thorocotomy. The retractor has a pair of arms movable toward and away from each other and a pair of blades mounted to the arms which may be placed in a chest incision. The blades have contact surfaces facing away from each other which engage the opposing sides of the incision to allow retraction thereof. The arms preferably are mounted to a rack having a plurality of teeth, and at least one of the arms has a pinion gear which engages the teeth on the rack to facilitate movement of one arm relative to the other. In other embodiments, a cable-drive mechanism may be used rather than a rack and pinion, or the arms may be mounted directly to each other or to a third member by a rotational joint.

In a preferred embodiment, a rail is disposed on each arm of the retractor, and, if the two arms are connected to a rack, a rail is also disposed on the rack. Various accessory components may be coupled to the rails, including heart stabilizers, heart retractors and manipulators, CO2 blowers, irrigators, suction devices, vascular clamps, lighting devices, catheters, and other devices. The rails are configured to allow slidable movement of such accessories components along the arms to a selected position.

The system of the invention will further include a stabilizer for stabilizing a surface of the heart. The stabilizer mounts to the retractor at any of various locations, preferably to one of the rails on the arms or rack of the retractor. The stabilizer includes a shaft and a foot, the foot being configured to atraumatically engage the surface of the heart to stabilize the surface while the heart is beating. The foot may have various configurations, including a bifurcated fork, partial or complete ring, or polygon, but will be suitable for stabilizing the heart adjacent to an anastomosis site to enable anastomosis of a graft vessel to a coronary artery. The foot may have a friction-enhancing surface to improve grip and minimize migration on the epicardium, which may be textured, knurled, roughened, or covered or coated with a friction-enhancing material. In a preferred embodiment, the foot is attached to the shaft by an articulating joint which may be locked and unlocked by means of an actuator coupled to the proximal end of the shaft. This allows the foot to be positioned at various orientations relative to the shaft according to the angle of approach and the location of the anastomosis site on the heart.

The stabilizer may optionally include one or more retainers which can be used for placement of sutures or silastics during an anastomosis or other procedure. The retainers are preferably located on the foot itself for proximity to the surgical site. The retainers are configured to retain the sutures or silastics in a state of tension, and have a clamping mechanism or are dimensioned for frictional engagement with the suture or silastic. In some embodiments, the retainers are removably attached to the stabilizer foot to allow the retainers to be removed when not needed or to be disposed of following the procedure.

The stabilizer is coupled to a mounting base which attaches to the rails of the retractor. The mounting base preferably includes at least two movable joints between the point of attachment to the rail and the point of attachment to the stabilizer, each joint having at least two axes of rotation. Preferably, the joints are spherical joints or ball-in-socket joints, thus maximizing the number of degrees of freedom available for positioning the stabilizer. The mounting base includes a coupling which attaches to the retractor rails, allows sliding movement thereon, and has a locking mechanism for locking the mounting base in a selected position on the rail.

The system may include a variety of other components and accessories useful in heart surgery. These include a heart retractor, which has a shaft, preferably malleable, and a paddle for engaging the heart. The paddle is preferably coated with a gauze or other atraumatic, friction-enhancing material to improve grip on the surface of the heart so as to facilitate rolling or lifting the heart. The system may also include a CO2 blower for emitting gas at the anastomosis site so as to keep it dry, clear of fluid and debris and thus visible to the surgeon. The blower preferably attaches to or is integrated into the stabilizer to facilitate positioning the blower outlet near the anastomosis site. A vascular clamp may also be provided which attaches to the rails of the retractor. The clamp may be used to temporarily clamp the end of a graft vessel such as the internal mammary artery and to hold it out of the surgical field until the surgeon is ready to use it. Various other devices may also be attached to the rails or other components of the system, including lighting, irrigation, suture retention, and retraction devices, as well as catheters and surgical instruments.

Referring now to the figures, FIG. 1 illustrates a first embodiment of a system for performing heart surgery according to the invention. The system includes a retractor 20 having a crossbeam 22, a stationary arm 24, and a movable arm 26. Stationary arm 24 and movable arm 26 have rails 28, 29 disposed along the top surface thereof, rails 28, 29 being defined by a pair of opposing side channels 30 forming a pair of lips 32 along the outer and inner upper edges of arms 24, 26. Stationary arm 24 and movable arm 26 further include wings 34, 36 extending outwardly from the lateral sides thereof. A plurality of channels 37 extend transversely across the top surfaces of stationary arm 24 and movable arm 26 and are dimensioned and configured for receiving a suture therein for retraction of the pericardium or other tissues, as described more fully below.

Movable arm 24 is attached to a carriage 38 slidably mounted to crossbeam 22. A key 40 is rotatably mounted to carriage 38 and is coupled to a pinion gear (described below) which engages a rack (described below) on crossbeam 22. In this way, movable arm 26 is movable toward and away from stationary arm 24 by rotating key 40. While stationary arm 24 is preferably mounted to crossbeam 22 so as to be unmovable, in some embodiments, both arms may be movably mounted to crossbeam 22 in the manner described above or in any other suitable manner. Crossbeam 22 further includes a pair of side channels 42 on its front and back edges each defining an upper lip 44 and a lower lip 46, thus forming a rail similar in construction to rails 28, 29 on stationary arm 24 and movable arm 26.

Figure 2:
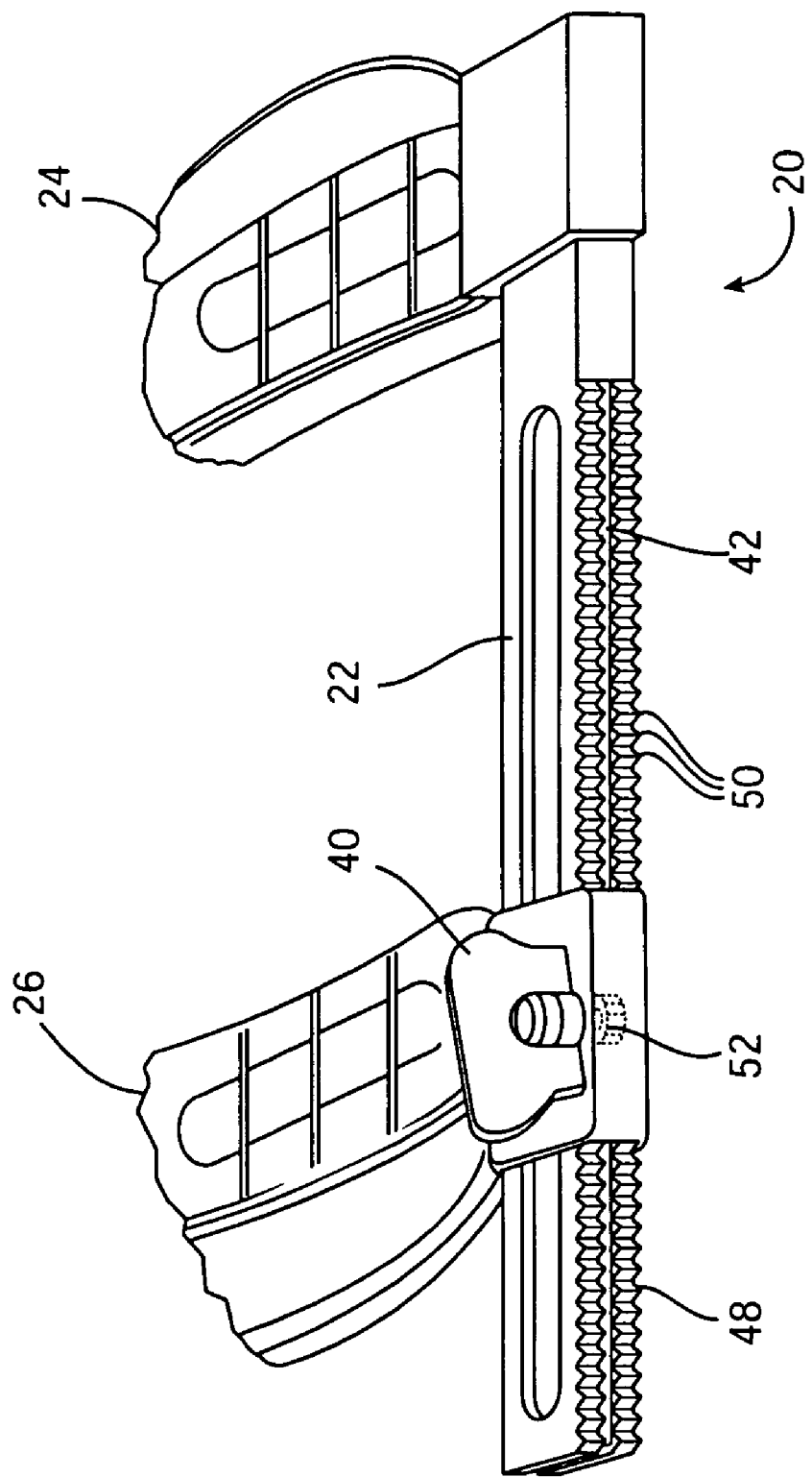
FIG. 2 is a partial perspective view of a retractor in the system of FIG. 1 showing a back side thereof.

Referring to FIG. 2, the back edge of crossbeam 22 forms a rack 48 having a plurality of linearly arranged gear teeth 50. Key 40 is coupled to a pinion gear 52 (shown in phantom) which engages rack 48, thus enabling movement of movable arm 26 by rotation of key 40. Side channel 42 extends longitudinally through rack 48, thus forming two parallel rows of gear teeth 50.

Figure 3:
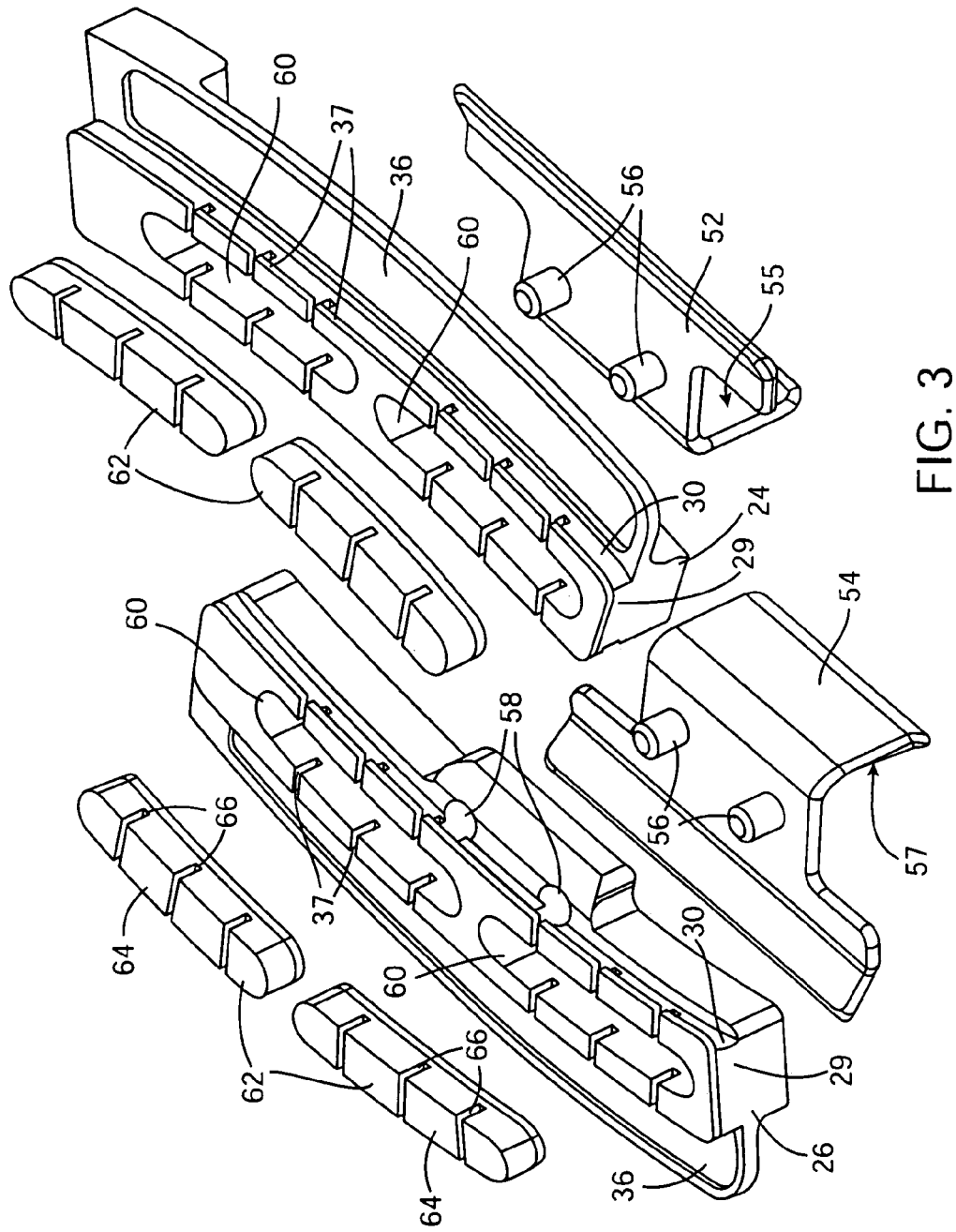
FIG. 3 is an assembly view of a stationary arm and a movable arm in the system of FIG. 1.

Referring again to FIG. 1, a first blade 52 is attached to stationary arm 24 and a second blade 54 is attached to movable arm 26. Preferably, first and second blades 52, 54 are removably coupled to arms 24, 26 to allow removal and interchange of various blades. As shown in FIG. 3, in which stationary blade 24 and movable blade 26 are shown removed from crossbeam 22 for clarity, first and second blades 52, 54 each have a pair of pins 56 which are slidably received in holes 58 in stationary arm 24 and movable arm 26. In this way, blades of various sizes and shapes may be easily interchanged according to the particular patient and procedure in which the device is being utilized. Blades 52, 54 have outwardly facing surfaces 55, 57 configured to atraumatically engage tissue or bone for retraction thereof.

In a preferred embodiment, crossbeam 22, stationary arm 24, movable arm 26, and first and second blades 52, 54 are all made of a biocompatible and sterilizable metal such as stainless steel, aluminum or titanium to allow resterilization and reuse after each procedure. However, it should be noted that any of these components may be made of an inexpensive material suitable for mass production, such as plastic, so that such components may be disposed of after a single use. In another exemplary embodiment, crossbeam 22 is metal so as to be reusable, while arms 24, 26 are plastic for single use and are removably attached to crossbeam 22 and carriage 38, respectively. Alternatively, crossbeam 22 and arms 24, 26 may be a reusable metal, while blades 52, 54 are a disposable plastic for single use.

Figure 4A:
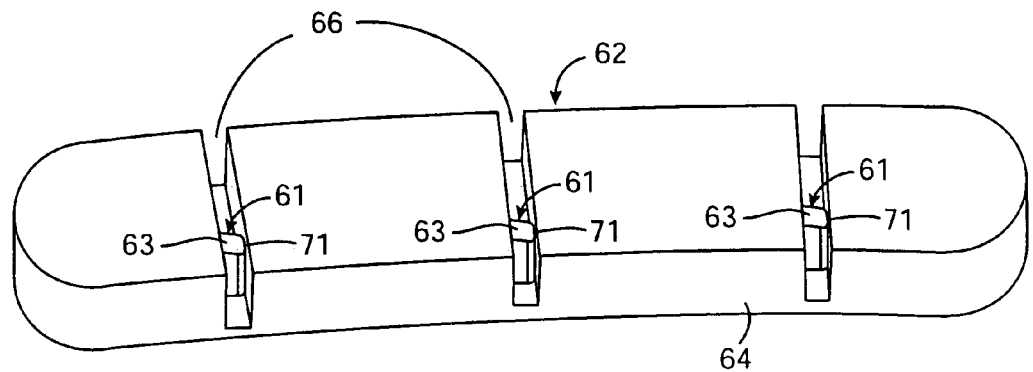
FIGS. 4A–B are top perspective and bottom perspective views, respectively, of a suture stay in the system of FIG. 1.
Figure 4B:
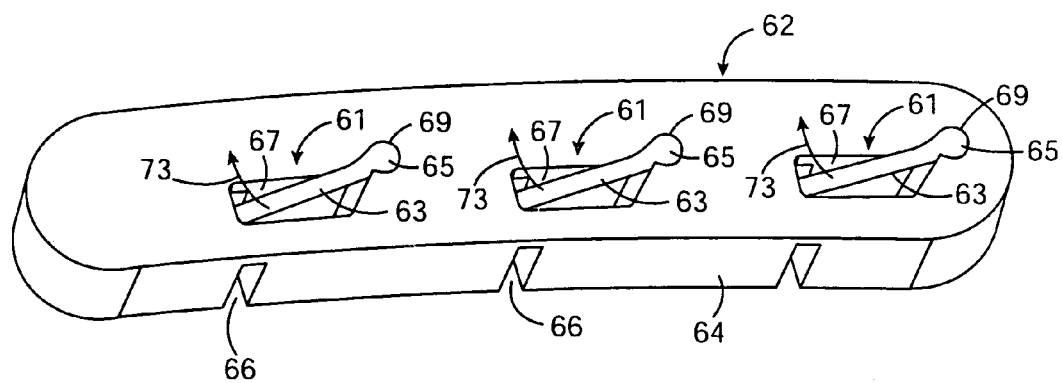
Figure 5:
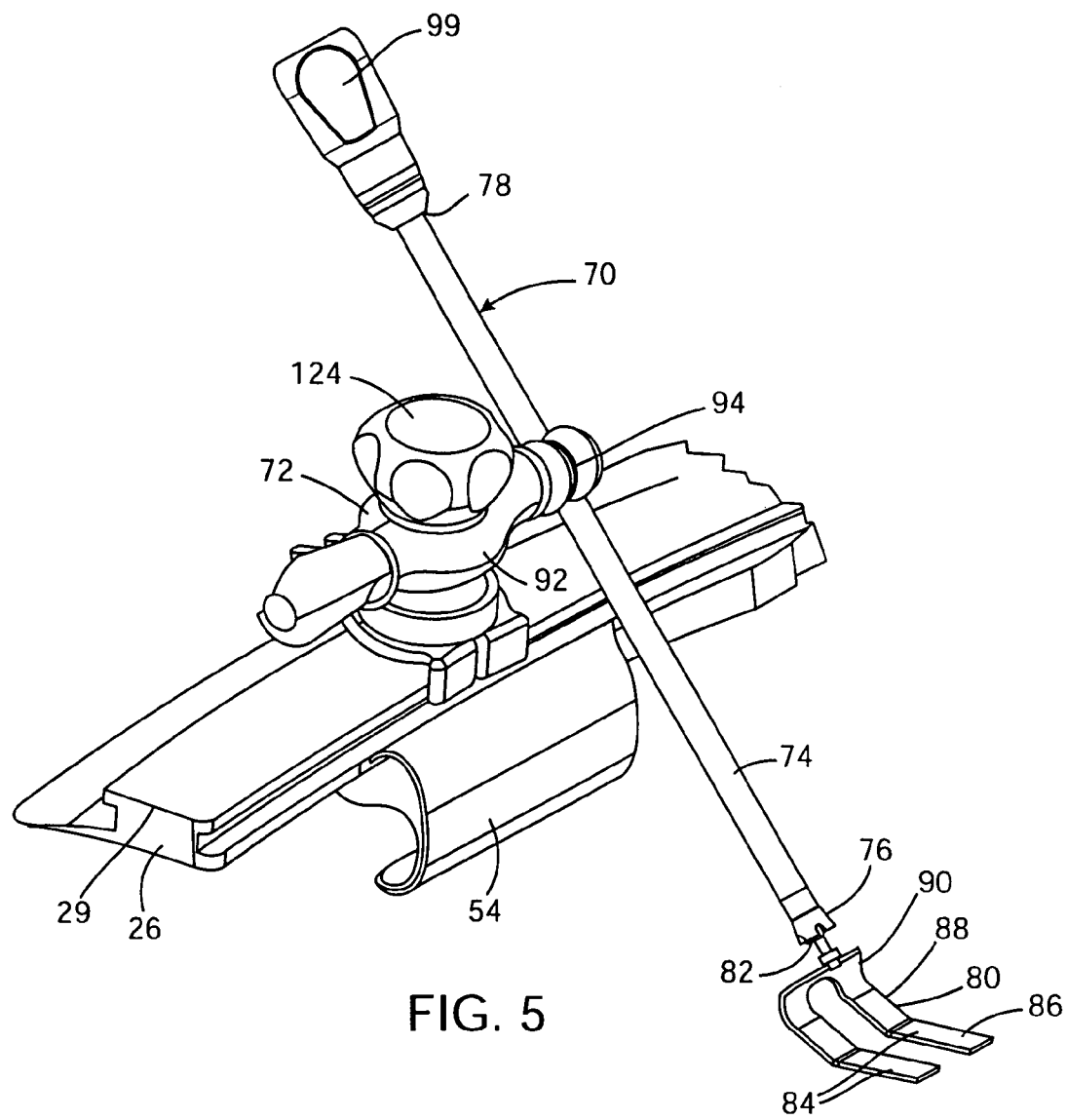
FIG. 5 is a perspective view of a stabilizer and mounting base mounted to an arm in the system of FIG. 1.
Figure 6:
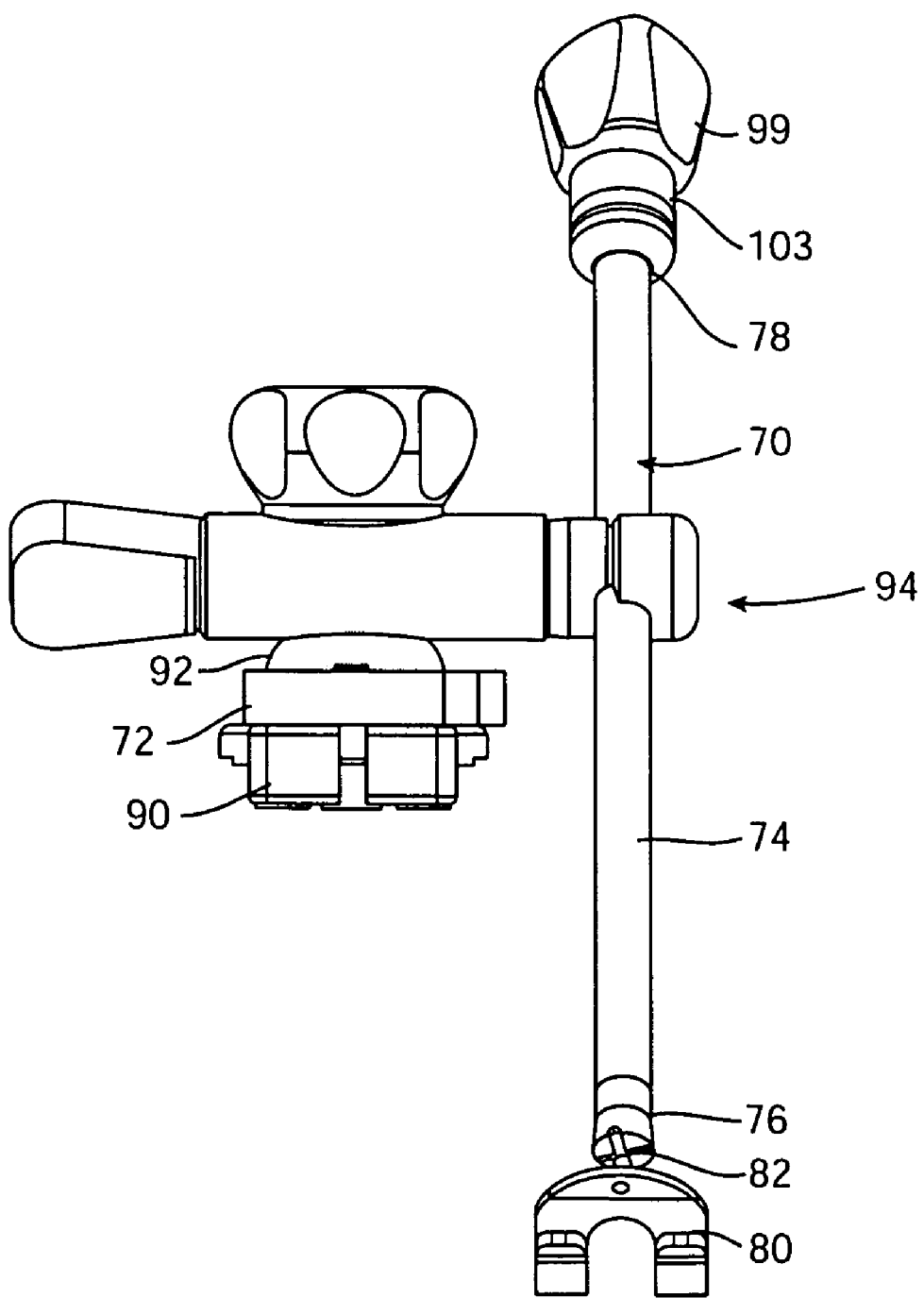
FIGS. 6–8 are front, side and top views, respectively, of the stabilizer and mounting base of FIG. 5.

Also shown in FIG. 3 are recesses 60 in the top surfaces of stationary arm 24 and movable arm 26 which are configured to receive suture stays 62. Suture stays 62 include a body 64 shaped for insertion into recess 60 and a plurality of slots 66 which align with channels 37 in arms 24, 26. As shown in FIGS. 4A–B, a clamp 61 is coupled to body 64 adjacent to each slot 66 and is configured to engage and retain a suture thread within slot 66. In an exemplary embodiment, each clamp 61 comprises a leaf 63 extending from a post 65. On the bottom side of body 62, an aperture 67 is disposed generally transverse to each slot 66 and has a bore 69 adjacent thereto. Posts 65 fit into bores 69, and leaves 63 are deflected so as to fit into apertures 67. In this way, leaves 63 are pre-loaded and biased into a clamping position in which their outer edges 71 are in engagement with the walls of slots 66. Outer edges 71 are deflectable in the direction of arrows 73 to allow a suture to be drawn into slots 66, but are biased back into engagement with the suture to clamp it in place.

Returning to FIG. 1, the system of the invention further includes a stabilizer 70 for stabilizing the surface of the heart or other organ during a surgical procedure. Stabilizer 70 may be mounted either to rails 28, 29 or to crossbeam 22 by means of a mounting base 72. As shown more clearly in FIGS. 5–8, stabilizer 70 includes a shaft 74 having a distal end 76 and a proximal end 78. A foot 80 is pivotably mounted to distal end 76 by means of a ball joint 82. Foot 80 is configured to engage the surface of the heart on opposing sides of an anastomosis site, preferably having a pair of arms 84 generally parallel to each other and spaced apart by a distance in the range of about 1–5 cm. Arms 84 have a generally flat portion 86 for engaging the heart, an angled portion 88 sloping upwardly from flat portion 86, and a proximal portion 91 which connects arms 84 and may have a curved, angled, or other suitable shape for attachment to a stem 92 coupled to ball joint 82. the bottom surfaces of arms 84 are adapted for atraumatic engagement with the epicardium, usually being smooth and flat. In a preferred embodiment, a friction-enhancing element is disposed on the bottom surfaces of flat portions 86. For example, the bottom surfaces may be textured with grooves, ribs, knurling, projections or other features, or they may be coated or covered with a friction-enhancing material such as foam, DACRON gauze, no-slip material, or a roughened or textured metal or plastic plate. Such material will enhance friction with the epicardium sufficiently to prevent slippage and migration of the foot, but not to such an extent as to injure the epicardial tissue.

Figure 7:
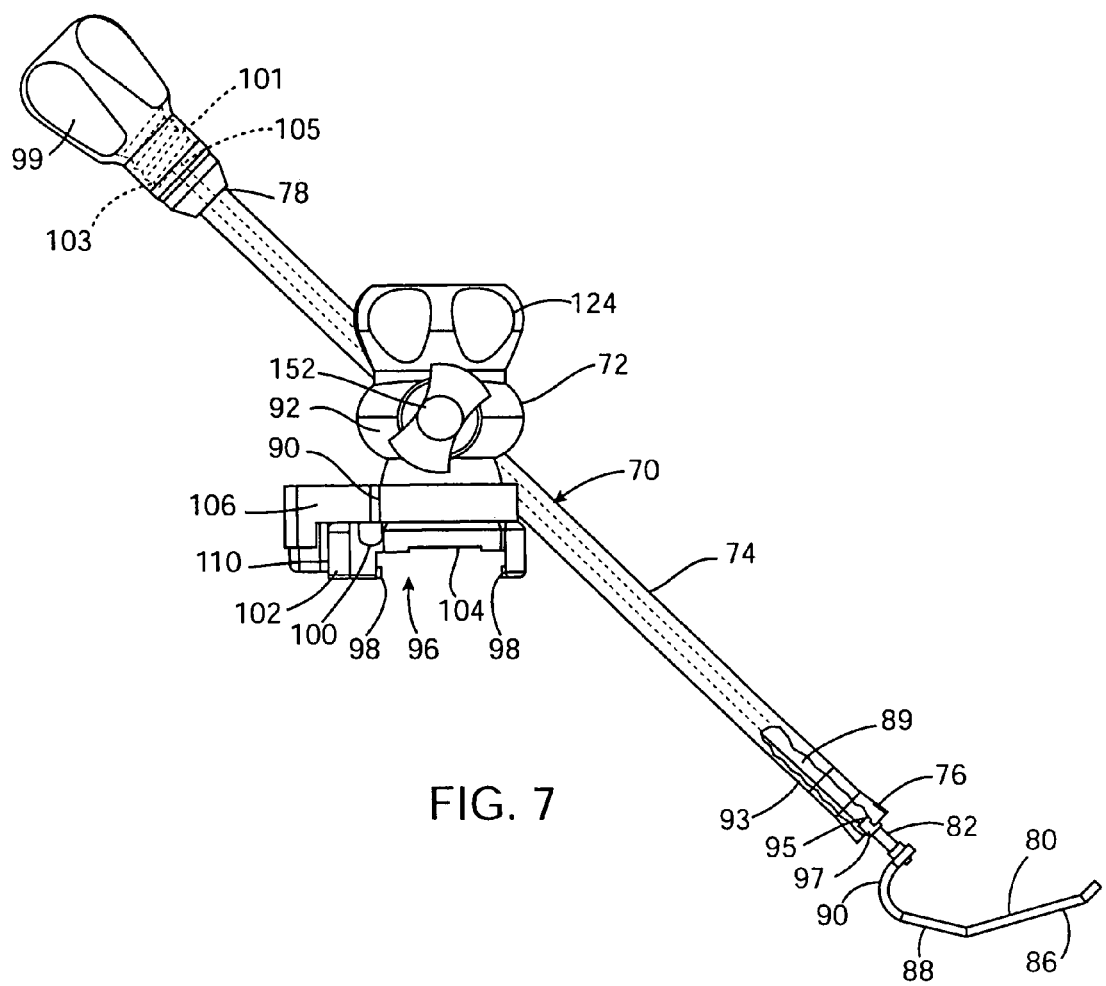
Figure 8:
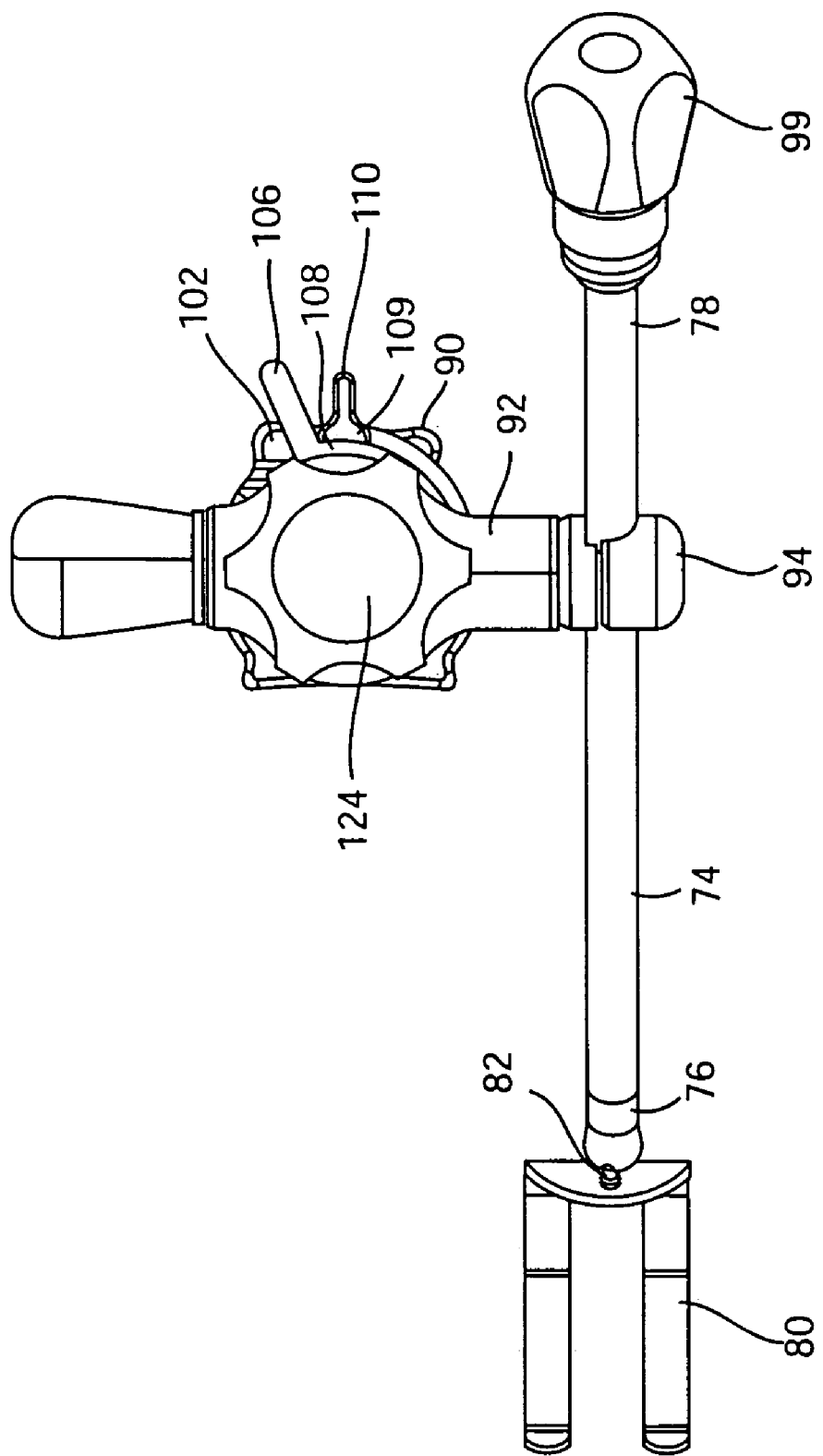

For purposes of locking foot 80 in a selected position relative to shaft 74, a rod 89 is slidably disposed within a channel 93 in shaft 74, as shown in FIG. 7. Rod 89 has a distal end 95 which engages ball 97 of ball joint 82. An actuator on the proximal end of shaft 74 has a rotatable knob 99 having a threaded body 101 which is received in a threaded socket 103 attached to shaft 74. A distal end of threaded body 101 is attached to proximal end 105 of rod 89. In this way, rotation of knob 99 drives rod 89 distally into tight, locking engagement with ball 97, thus locking foot 80 in position.

It should be understood that stabilizer 70 and foot 80 may have various other configurations and features. For example, foot 80 may have an annular ring shape or angular polygonal shape, or have simply a single heart-engaging arm. Stabilizer 70 may further have a suction lumen and suction holes or cups on the bottom surface of foot 80 in order to apply suction to the epicardium for enhanced stability and immobility. Other features and configurations may also be provided, such as those described in U.S. Pat. No. 5,807,243, assigned to the assignee of the present application and hereby incorporated herein by reference.

Mounting base 72 includes a carriage 90 adapted for slidable engagement with rails 28, 29, a turret 92 rotatably mounted to carriage 90, and a clamp 94 rotatably mounted to turret 92. Carriage 90 has a channel 96, as shown in FIG. 7, configured to slide onto rails 28, 29 or crossbeam 22. Channel 96 has a pair of inwardly projecting lips 98 configured to be positioned within side channels 30 in arms 24, 26 or side channels 42 in crossbeam 22. For the purpose of clamping carriage 90 in a selected position along rails 28, 29 or crossbeam 22, carriage 90 has a living hinge 100 which allows an outer portion 102 of carriage 90 to rotate toward and away from an inner portion 104. A lever 106 is rotatably mounted to carriage 90 and has a sloped cam 108 which engages a camming surface 109 on outer portion 102 so as to urge it toward inner portion 104 as lever 106 is actuated in the clockwise direction (see FIG. 8). This locks carriage 90 in place along rails 28, 29 or crossbeam 22. Rotating lever 104 in the opposite direction allows outer portion 102 to rotate away from inner portion 104, thus allowing carriage 90 to be slid along or removed from rails 28, 29 or crossbeam 22. A stationary finger grip 110 is mounted to outer portion 102 of carriage 90 to enhance leverage during actuation of lever 104.

Figure 9:
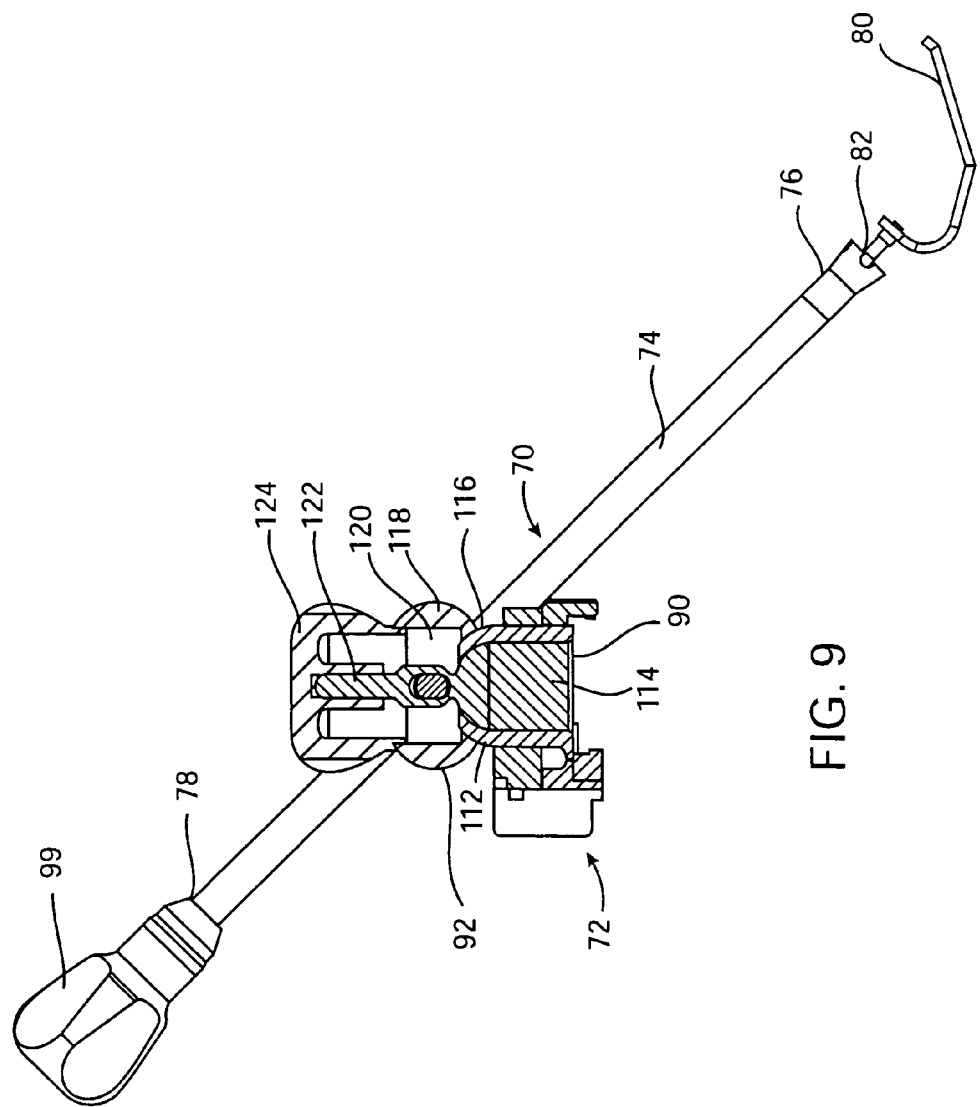
FIG. 9 is a side cross-section through the mounting base of FIG. 5.

Referring to FIG. 9, turret 92 preferably provides rotation about at least two axes. In an exemplary embodiment, turret 92 comprises a spherical joint 112 having a base 114 attached to carriage 90 with a hemispherical top surface 116, and a socket 118 having a cavity 120, whereby socket 118 is rotatable about multiple axes relative to base 114. In order to secure socket 118 in a given position relative to base 114, a threaded post 122 is secured to base 114, extends upwardly through socket 118 and is coupled to a threaded cap 124 having a lower end in engagement with socket 118. In this way, socket 118 may be locked in a selected position by tightening cap 124 on post 122, thus pressing socket 118 into engagement with base 114.

Figure 10:
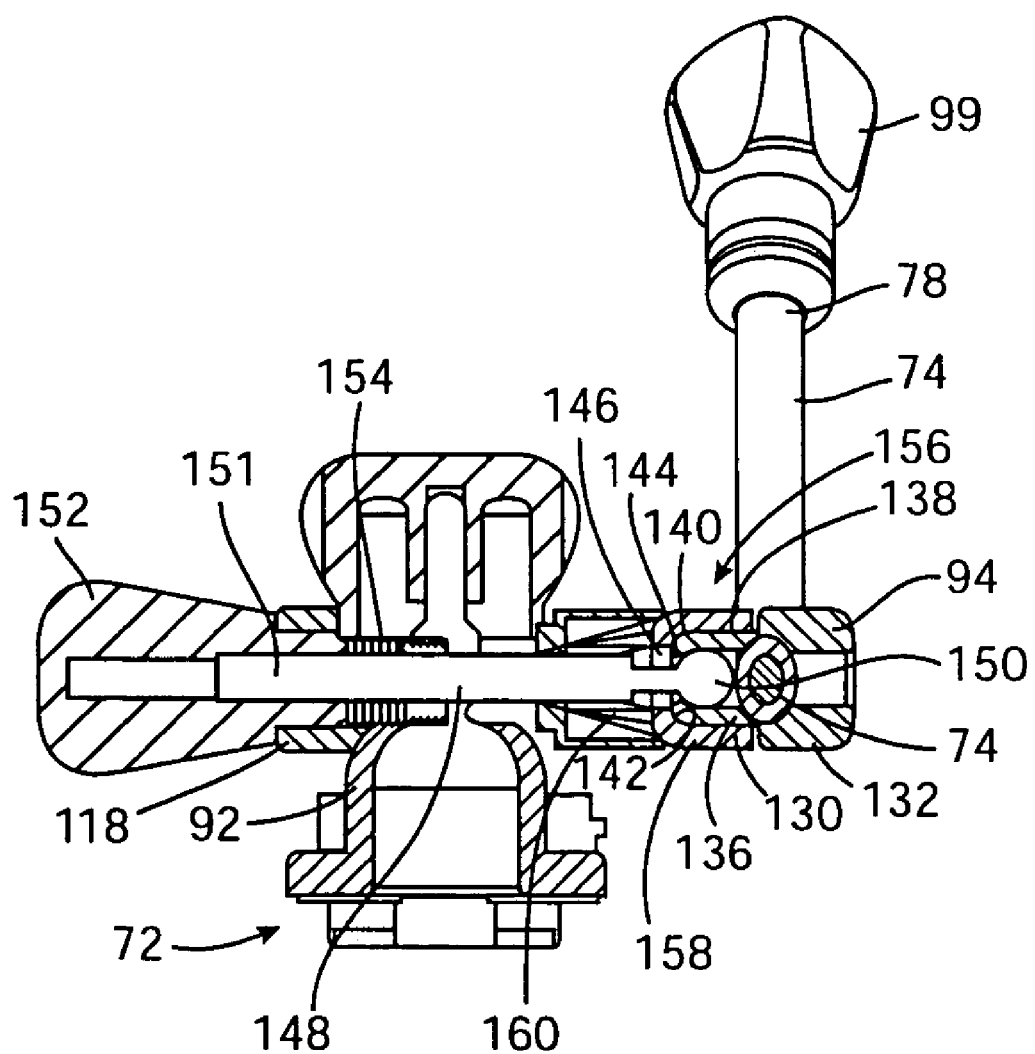
FIG. 10 is a front cross-section through the mounting base of FIG. 5.

Referring to FIG. 10, clamp 94 is configured to hold shaft 74 of stabilizer 70, or any of various other surgical instruments and devices utilized with the invention. Like turret 92, clamp 94 preferably provides rotation about at least two axes. In an exemplary embodiment, clamp 94 has an inner member 130 and an outer member 132. Outer member 132 has a bore 134 in which shaft 74 is slidably positioned. A cylindrical extension 136 on outer member 132 is slidably received within a cavity 138 in inner member 130. Cylindrical extension 136 has a tapered inner end 140 which engages a tapered surface 142 in cavity 138. Tapered inner end 140 has an opening 144 and inner member 130 has an opening 146 through which a rod 148 extends. Rod 148 has a ball 150 on its outer end which resides within cylindrical extension 136 and is retained therein by tapered inner end 140, opening 144 being smaller than ball 150. Rod 148 extends through socket 118 of turret 92 and has a threaded end 151 opposite ball 150. A threaded knob 152 engages threaded end 151, allowing outer member 132 to be drawn toward inner member 130 by rotating knob 152, thus clamping shaft 74 in bore 134. A spring 154 is disposed around threaded end 151 and engages knob 152 urging it outwardly. This provides a small amount of clamping force on shaft 74 even when knob 151 is loosened, preventing the inadvertent slippage of stabilizer 70 into the surgical site.

Clamp 94 preferably also includes a spherical joint 156 to provide additional degrees of freedom for positioning stabilizer 70. Inner member 130 has a hemispherical outer end 158 which is received in a clamp socket 160 attached to socket 118 of turret 92. Clamp socket 160 may be a conical, spherical, or otherwise tapered concavity allowing rotation of inner and outer members 130, 132 about multiple axes relative to turret 92. Opening 146 in inner member 130 has tapered edges and is sufficiently large to allow a wide range of rotational movement of inner member 130 about rod 148. Spherical joint 156 is locked in a selected position in the same way as clamp 94, by tightening knob 152, which pulls on rod 148 thus urging inner member 130 into tight engagement with clamp socket 160.

Figure 16:
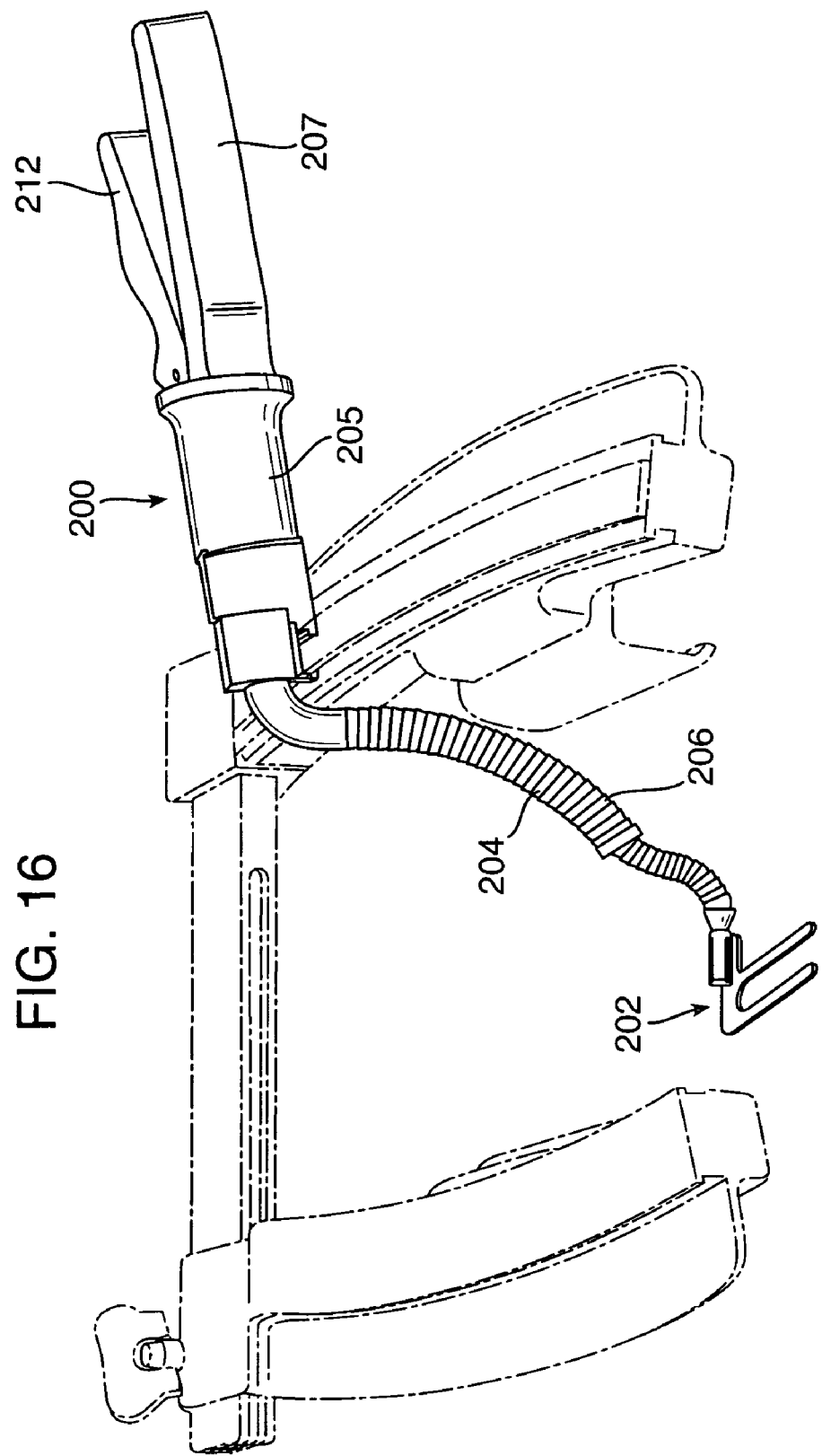
FIG. 16 shows another stabilizer according to the present invention.
Figure 19:
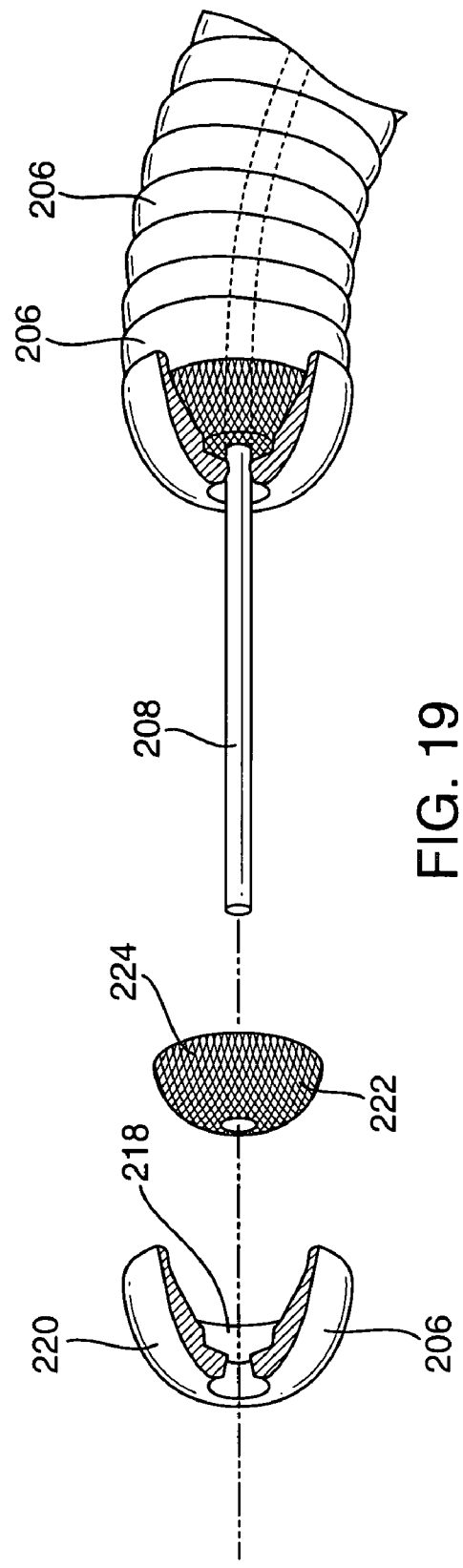
FIG. 19 is an exploded view of the flexible arm showing the links and a friction enhancing layer.

Referring to FIGS. 16 and 19, another stabilizer 200 is shown with the retractor 20. The stabilizer 200 is preferably used with the retractor 20 but may, of course, be used with any other retractor. Furthermore, although the retractor is designed for use with a median sternotomy, the stabilizer 200 may be used with retractors in other parts of the chest and specifically with smaller, less-invasive openings, without departing from the scope of the invention.

The stabilizer 200 has a foot 202 coupled to a flexible arm 204. The foot 202 may be any foot described herein or any other suitable foot. The flexible arm 204 is formed by a number of links 206 which permit the arm 204 to bend and deform. An elongate element 208, such as a cable 210 or wire, extends through the links 206. A base link 228 permits the arm 204 to be initially directed in different directions in the manner described below. When the elongate element 208 is tensioned to a locked position, the links 206 are drawn together so that the frictional engagement between the links 206 locks the arm 204. Tension is reduced to permit the links 206 to slide against one another and provide flexibility to the arm 204 when positioning the arm 204. In this manner, the arm 204 can be locked in a number of different orientations to reach different parts of the heart.

The stabilizer 200 has an actuator 212, which is preferably a manually actuated lever or trigger, movable from a natural position (FIGS. 16 and 17) to an actuated position (FIG. 18) upon actuation by the user. The actuator 212 is mounted to a body 205 having a handle 207. As will be explained below, an advantage of the stabilizer 200 of the present invention is that locking and unlocking of the arm 204 to the retractor 20, the arm 204 itself, the base link 228 and the foot 202 may be accomplished with the actuator 212. Of course, the actuator 212 may lock more or fewer of these features without departing from the scope of the invention.

Figure 17:
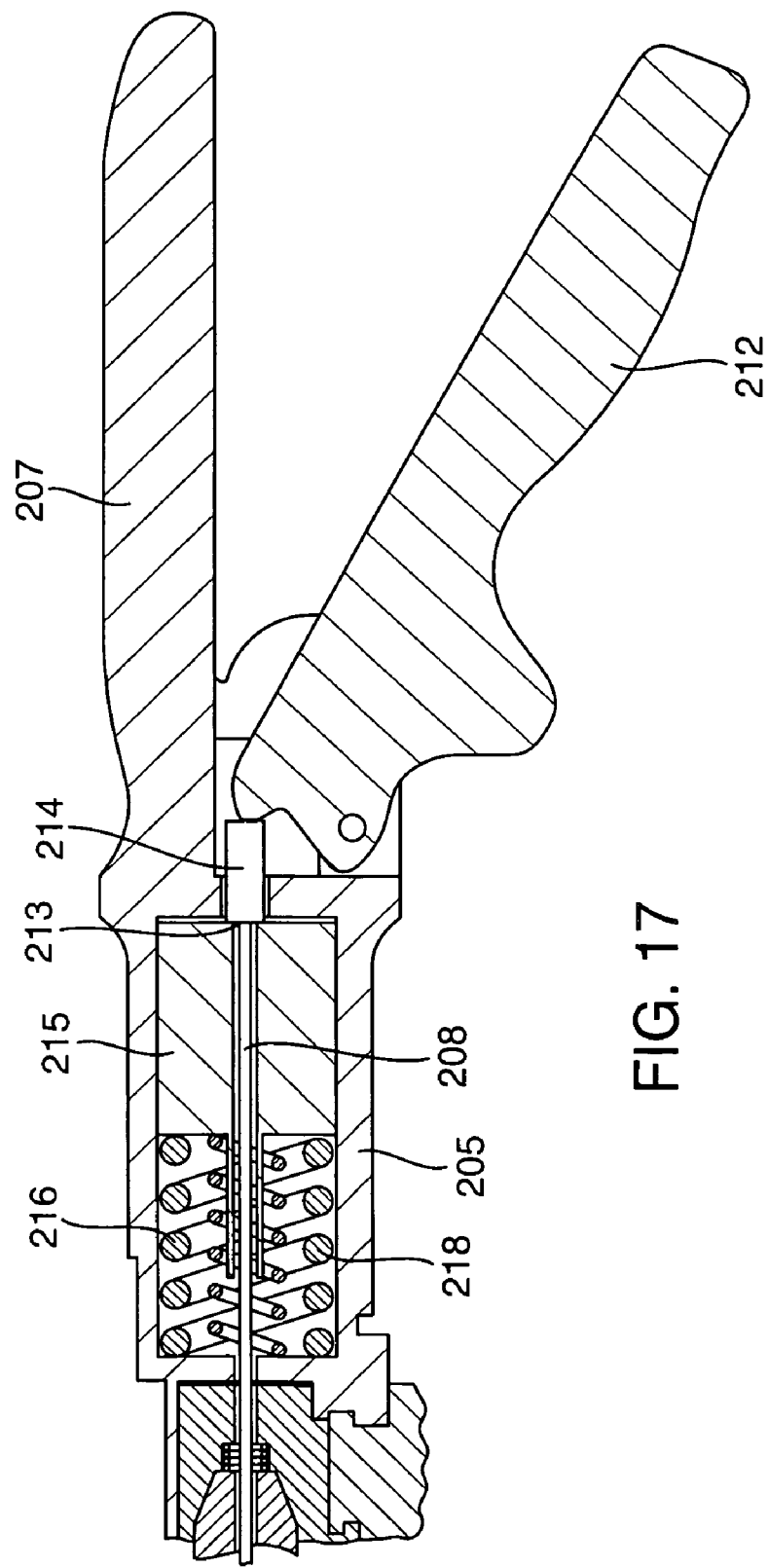
FIG. 17 shows the actuator biased into a natural position by a pair of springs.
Figure 18:
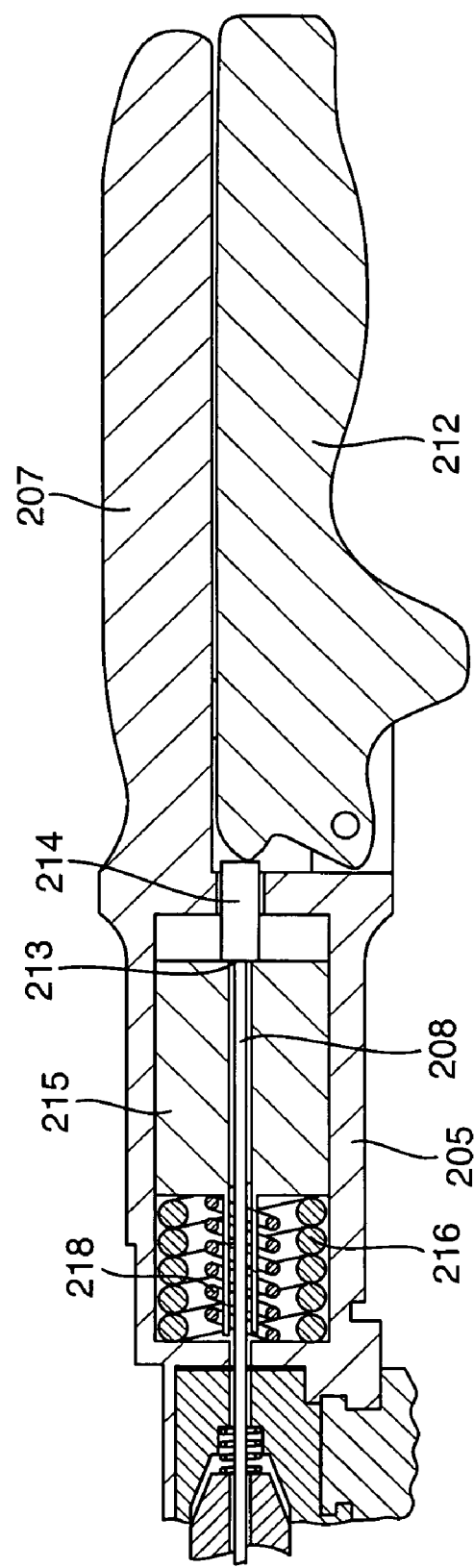
FIG. 18 shows actuation of the actuator against the force of the springs to unlock the flexible arm.

Referring to FIGS. 16–18, the elongate element 208 has an end 213 attached to a holder 214. The holder 214 is coupled to the actuator 212 with suitable connections to move the holder 214. The holder is also coupled to a block 215, which is acted on by a first and second springs 216, 218 although one or more springs may be used. The springs 216, 218 bias the actuator 212 in the locked position of FIG. 17 so that the arm 204 is normally locked. When the actuator 212 is actuated, the holder 214 moves proximally to reduce tension in the elongate element 208 thereby unlocking the arm 204.

An advantage of the present invention is that the actuator 212 is naturally biased to a position in which the arm 204 is locked. When the user is ready to move the foot 202, the actuator 212 is manipulated reduce tension on the elongate member 208 thereby unlocking the arm 204 and foot 202. The foot 202 and arm 204 are then moved to the desired position. The user then simply releases the actuator 212 and the springs 216, 218 automatically lock the arm 204, foot 202 and the stabilizer 200 to the rail 28 of the retractor 20. This provides advantages over many conventional devices which require positive actuation force to lock the arm 204 and/or foot 202. During actuation of such devices, the user may inadvertently move or displace a part of the device when applying the force required to actuate the actuator 212.

The present device, on the other hand, locks one or more features by simply releasing the actuator 212.

Referring to FIG. 19, the links 206 have a concave side 218 and a convex side 220. A friction enhancing layer 222 is positioned between adjacent links 206. The friction enhancing layer 222 is preferably a screen 224 made of stainless steel mesh but may be any other suitable structure. When the elongate element 208 is tensioned and the arm 204 is locked, the layer 222 produces high frictional resistance to sliding between adjacent links 206. The high frictional resistance limits such sliding to reduce looseness in the arm 204 when the arm 204 is locked. Reducing the amount of looseness in the arm 204 is particularly important when the arm 204 is used to stabilize a coronary artery. Small displacements in the links 206 can yield relatively large displacements at the distal end of the arm 204 which can be problematic when working on small vessels.

The layer 222 may be attached to a side of the link 206 such as to the convex side 220. In this manner, the convex side 220 is harder and more textured than the concave side 218. The layer 222 may also be embedded in the link 206 or may simply be a layer applied on the link 206. Of course, the layer 222 may be applied in any other manner to provide differing hardness and/or texture. The high frictional resistance produced by the layer 222 reduces the required tension in the elongate element 8 to lock the arm 204. In the preferred embodiment, the tension required to lock the arm is preferably less than 200 lbs., more preferably less than 150 lbs. and most preferably less than 120 lbs.

Referring to FIGS. 20–24, a proximal end 226 of the arm 204 is shown. The proximal end 226 of the arm 204 has a base link 228 which pivots relative to the body about a first axis 230. The base link 228 directs the elongate element 208 along a second axis 232 which is offset relative to the first axis 230. The second axis 232 preferably forms an angle of 45–90 degrees, preferably about 70 degrees relative to the first axis 230. In this manner, the base link 228 essentially directs the elongate element 208 along an arc when pivoted about the first axis 230. Of course, the base link may also direct the elongate element 208 essentially perpendicular to the first axis 230.

An advantage of the base link 228 is that the arm 204 can be initially directed toward a desired target area. Many conventional arms must bend around a relatively large bend radius before achieving the angle of attack that the base link 228 can provide over a short distance. The base link 228 extends relatively far from the first axis 230 which reduces the number of links 206 thereby, reducing looseness in the arm and the tension required to lock the arm 204. The base link 228 preferably extends a distance 247 of at least 0.3 inch and more preferably at least 0.5 inch from the first axis 230. Still another advantage of the base link is that adjustments in the position of the arm 204 may be accomplished by simply manipulating the arm 204 and the base link 228.

The base link 228 has a tapered surface 234 which mates with a tapered surface 236 on a first tooth 238. When tension is applied to the elongate element 208, the tapered surfaces 234, 236 engage one another to lock the base link 228 to the first tooth 238 and prevent pivoting of the base link 228. In this manner, the base link 228 is also locked against rotation when the elongate element 208 is tensioned. The tapered surface 234 preferably forms an angle of 20–60 degrees, more preferably 34–45 degrees and most preferably about 40 degrees relative to the first axis 230. A spring 240 biases the surfaces 234, 236 apart to ensure that the base link 228 is free to pivot when the arm 204 is unlocked.

Figure 20A:
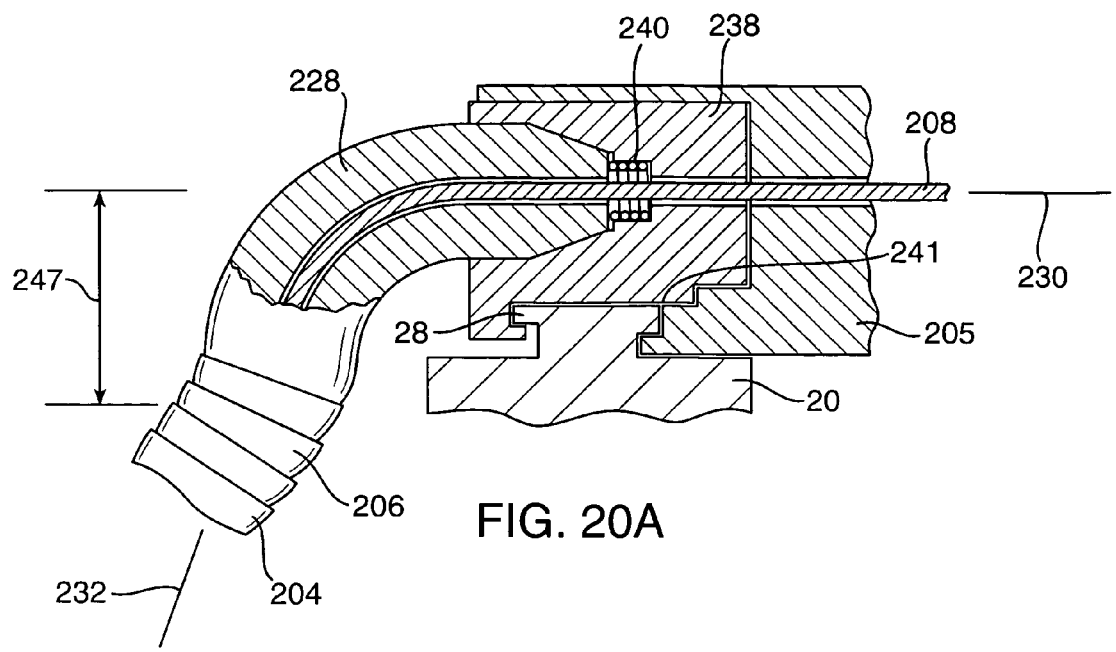
FIG. 20A is a cross-sectional view of a proximal end of the arm showing a base link locked to the body.
Figure 20B:
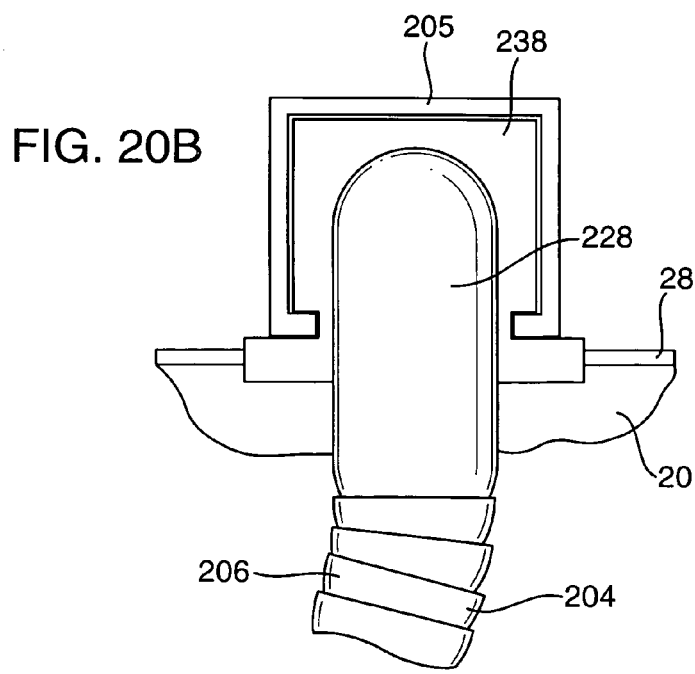
FIG. 20B shows the base link.
Figure 21:
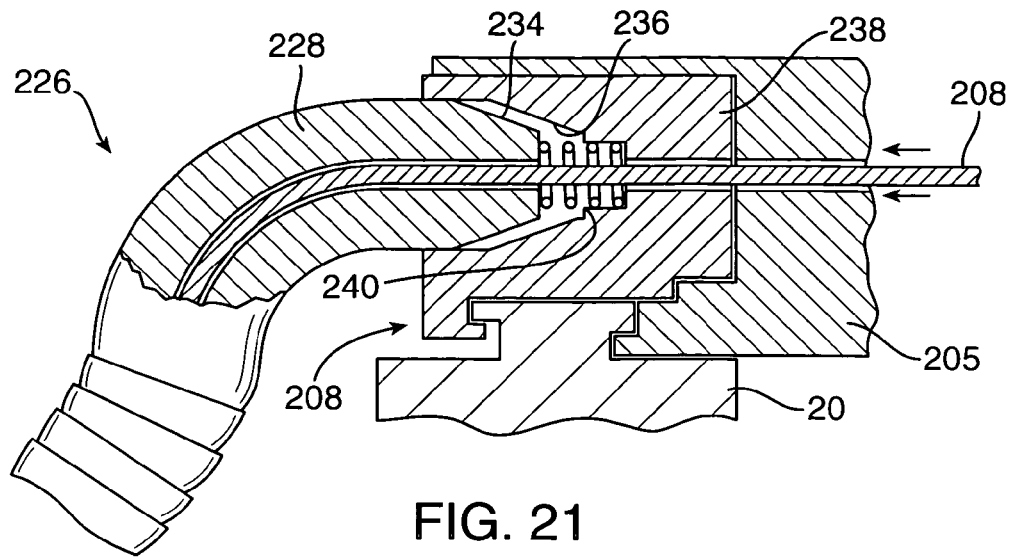
FIG. 21 is a cross-sectional view of the base link showing the base link free to pivot relative to the body.
Figure 22:
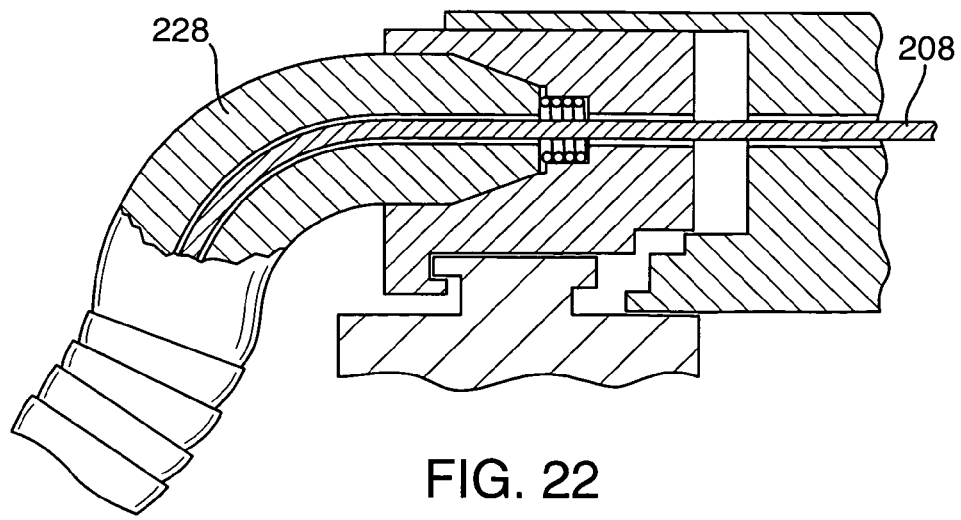
FIG. 22 is a cross-sectional view showing the base link with the body moved to separate the teeth.
Figure 23:
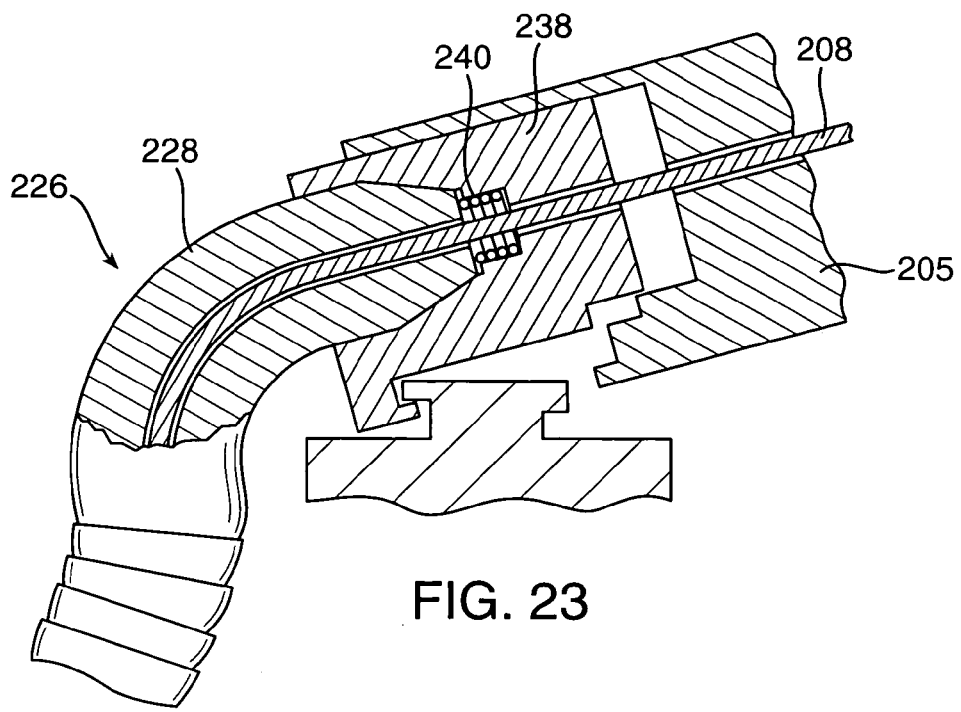
FIG. 23 shows the stabilizer partially removed from a rail on the retractor.
Figure 24:
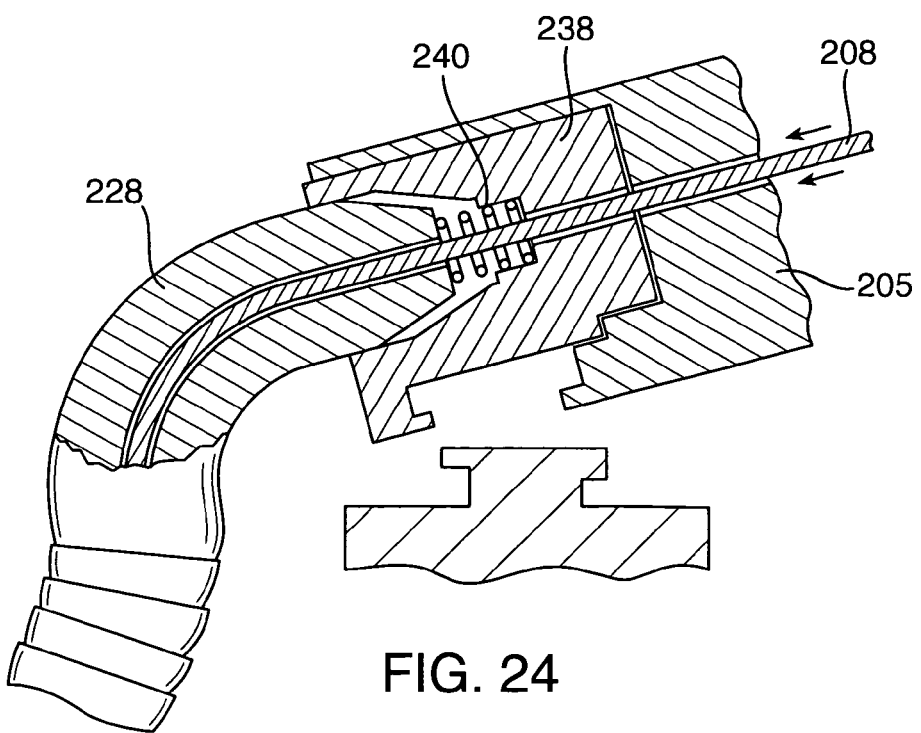
FIG. 24 shows the stabilizer completely removed from the retractor.

Still referring to FIG. 20, the arm 204 is locked to the retractor 22 with a locking mechanism 241. The locking mechanism 241 is also preferably locked and unlocked with the elongate element 208. When the elongate element 208 is tensioned to the locked position, tension in the elongate element 208 is transmitted from the base link 228 to the first tooth 238 thereby trapping the rail between the first tooth 238 and a second tooth 243 attached to the body 205. Referring to FIGS. 22–24, the body 205 is pulled to compress the spring 240 and permit the first and second teeth 238, 243 to spread apart far enough to release the stabilizer 200 from the retractor 20.

Referring to FIGS. 25–28, the foot 202 is pivotably and releasably attached to the arm 204 in the following manner. The foot 202 has a pin 242 extending into an opening 246 in a distal housing 248. The distal housing 248 is coupled to a distal link 250. A ball plunger 252 having a ball 254 engages a circumferential recess 256 in the pin 242. The engagement between the pin 242, ball plunger 252 and opening 246 permits pivoting the foot 202 and also permits the user to remove and replace the foot 202 with a moderate amount of force.

The pin 242 is locked against pivoting when the arm 204 is locked. The elongate element 208 extends through a hole 264 in a yoke 266 which slides within the distal housing 248. When the elongate element 208 is tensioned, the pin 242 is essentially clamped by the yoke 266, the sides 268 of the opening 246 in the distal housing 248 and the ball plunger 252. The yoke 266 is biased by a spring 270 which forces the yoke 266 distally into contact with the housing 248 to align the opening 246 and hole 264 when tension is reduced in the elongate element 208. A threaded plug 272 is positioned in a threaded recess 274 in the distal housing 248 to adjust alignment between the housing 248 and yoke 266 if necessary. The opening in the housing is preferably smaller toward the proximal end to wedge and clamp the pin in the opening 246. As mentioned above, the elongate element 208 is preferably tensioned at all times until the actuator 212 is actuated. In this manner, the foot 202 is unlocked and locked together with the arm 204.

Figure 28B:
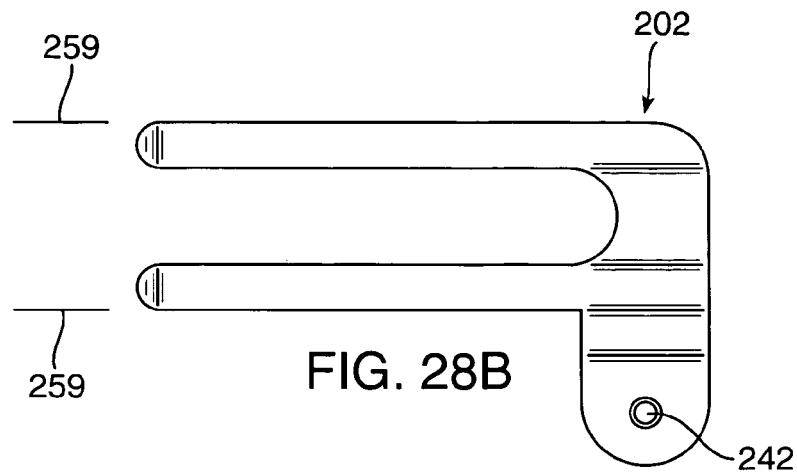
FIG. 28B is a plan view of the foot of FIG. 28A.
Figure 28A:
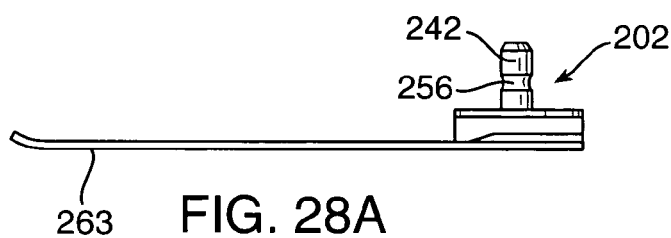
FIG. 28A is a side view of another foot.
Figure 27A:
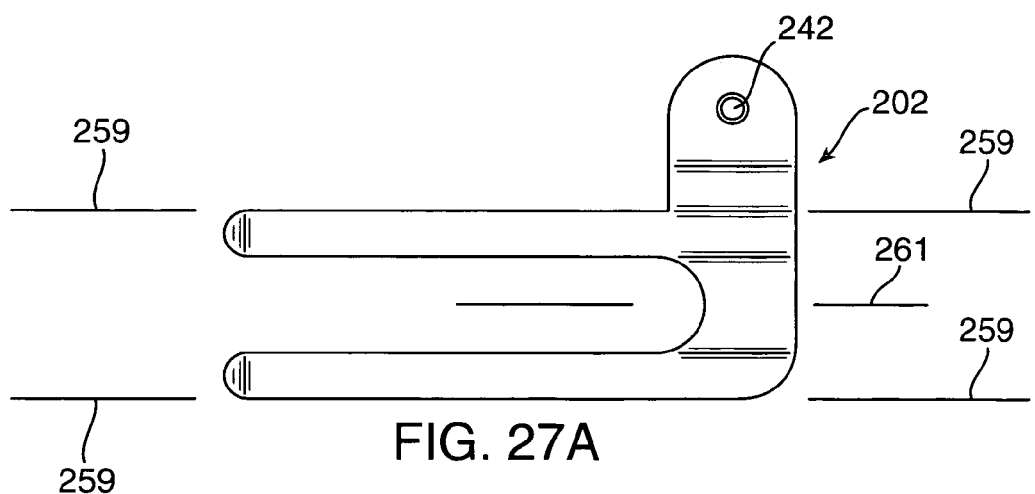
FIG. 27A is a plan view of the foot.
Figure 27B:
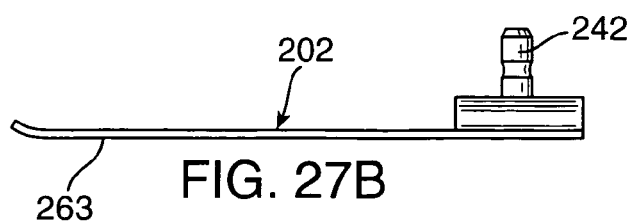
FIG. 27B is a side view of the foot of FIG. 27A.
Figure 29:
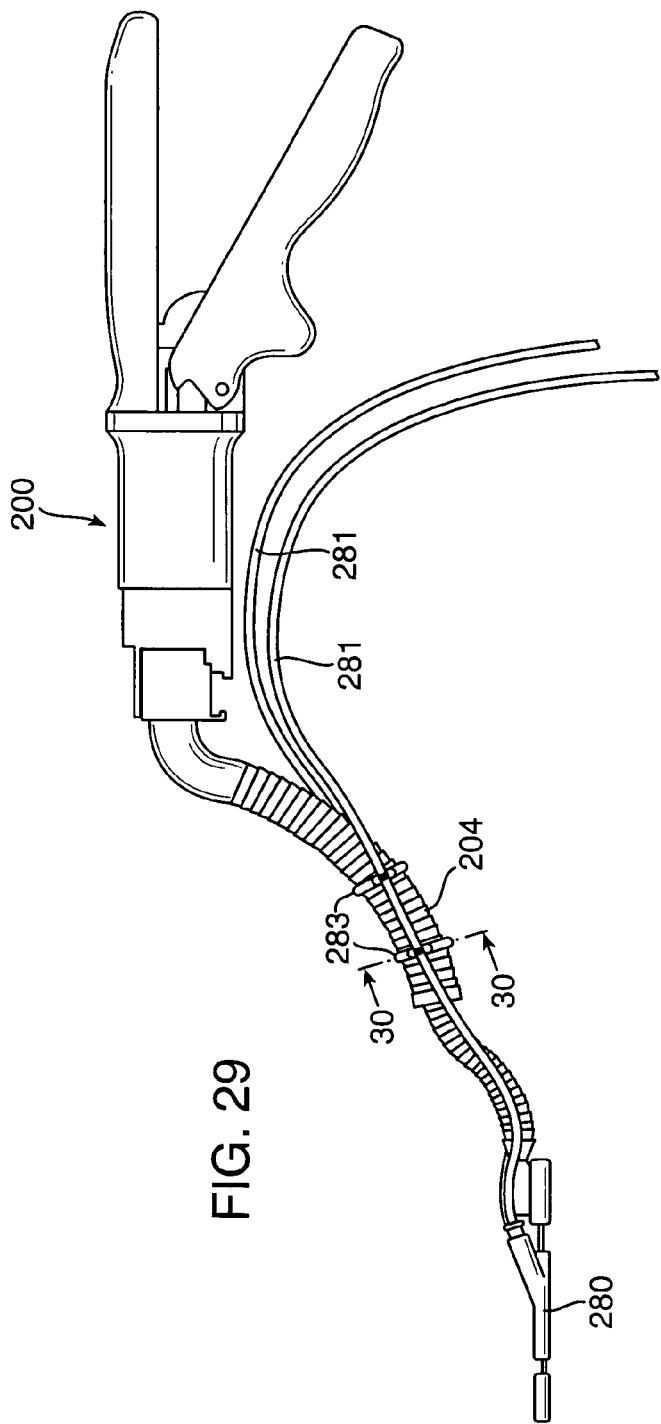
FIG. 29 shows the stabilizer holding a suction foot.
Figure 30:
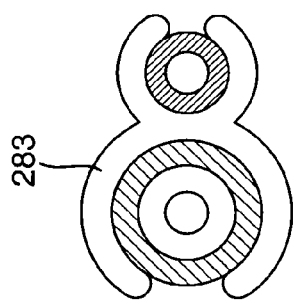
FIG. 30 shows a clip for holding a suction lumens leading to the suction foot.

The foot 202 pivots about an axis 258 which is non-collinear and preferably angled or offset relative to an axis 260 defined by a central axis 262 of the distal link 250 and/or the elongate element 208. In the preferred embodiment, the axis 258 forms an angle of 70–110 degrees and preferably about 90 degrees with the central axis 262 of the distal link 250 and/or the elongate element 208 which provides advantages when reaching various parts of the heart. Stated another way, the axis 258 is perpendicular to a bottom surface 263 of the foot 202 (FIG. 28A, FIG. 27B) but is offset relative to the axis 260. The axis 258 around which the foot 202 pivots is also preferably outside an area defined between imaginary lines 259 extending from first and second arms 263, 265. The first and second arms 263, 265 are preferably parallel but may be angled or malleable into various configurations as described below. Stated another way, the axis 258 is offset from a central axis 261 between the arms 263, 265 by at least 0.20 inch and more preferably at least 0.40 inch. In this manner, the connection between the arm 204 and the foot 202 are more easily positioned outside the surgical area. Another advantage of the invention is that the pin 242 can be placed on either side of the foot 202 as shown in FIGS. 27–28 and the user is preferably provided with at least removable and replaceable feet 202 having different shapes or mounting configurations. The pin 242 is preferably mounted to a raised part of the foot 202 which is preferably raised from the bottom surface 263 by at least 0.050 inch and more preferably at least 0.100 inch.

Referring now to FIGS. 29–35, a suction foot 280 is shown. The foot 280 has suction lumens 281 which provide suction to adhere the foot 280 to the surface of the heart. The foot 280 has suction recesses 282 coupled to the suction lumens 281. The suction lumens 281 are held to the arm 204 with clips 283 and attach to the foot 280 at connections 284. The foot 280 is preferably held by the stabilizer 200 and has a pin 242 to engage the stabilizer to provide the advantages described above. The foot 280 may, of course, be used with any other arm without departing from various aspects of the invention.

Figure 31:
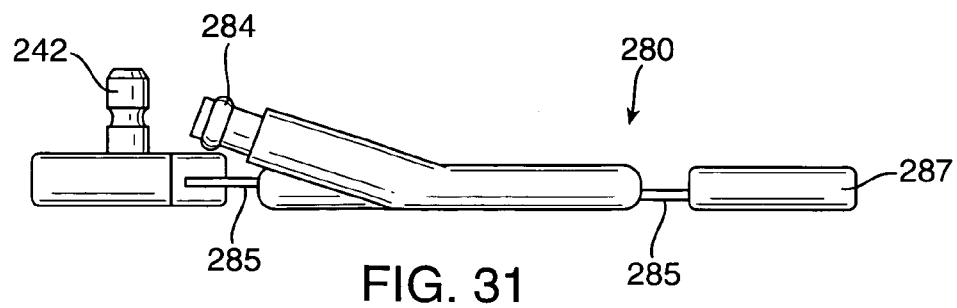
FIG. 31 shows a plan view of the suction foot.
Figure 32:
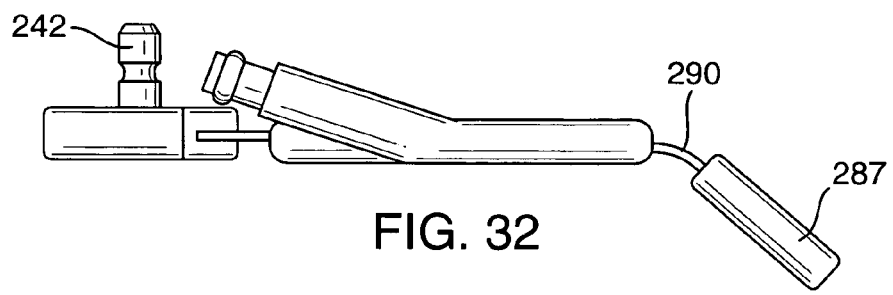
FIG. 32 shows the suction foot with the extensions displaced.
Figure 33:
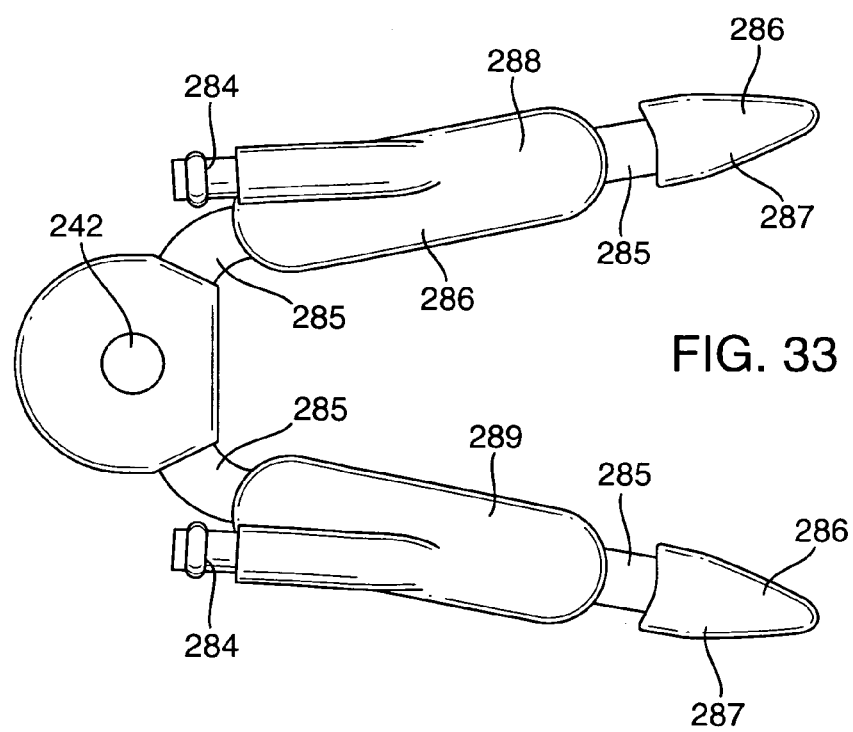
FIG. 33 shows the suction foot with the arms spread apart.
Figure 34:
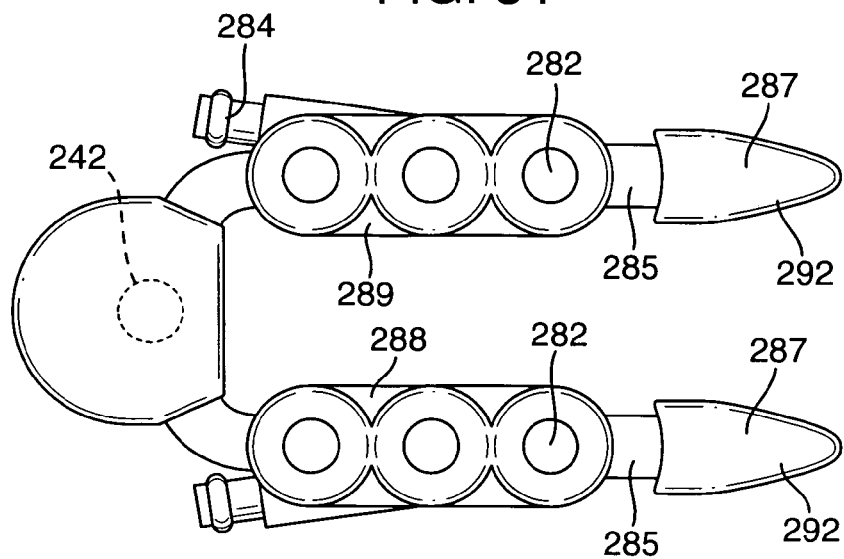
FIG. 34 shows the bottom of the suction foot.
Figure 35:
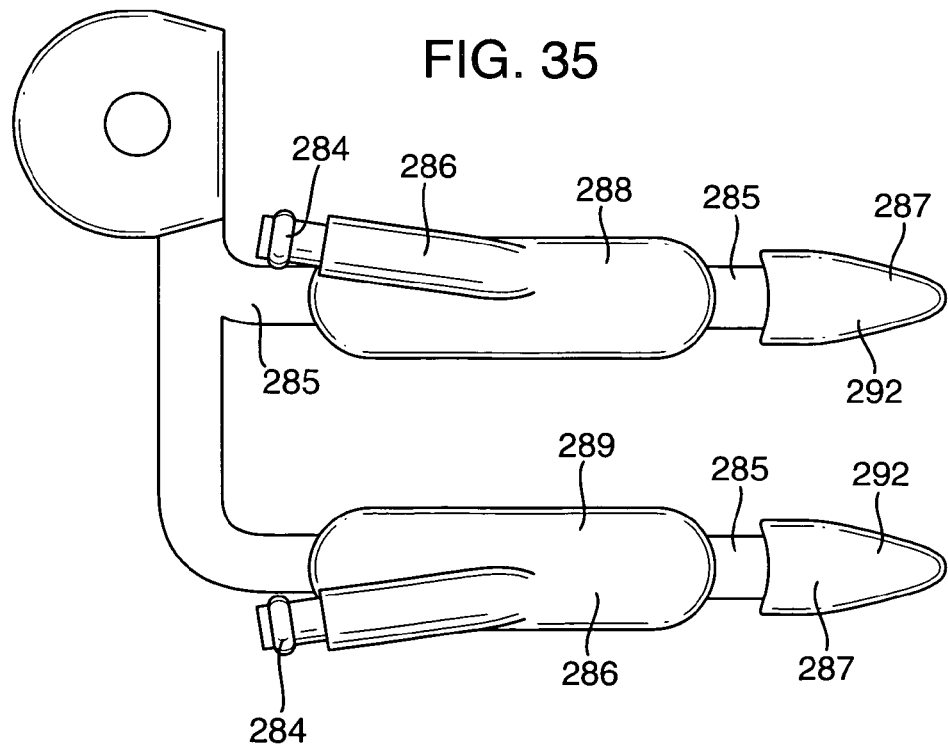
FIG. 35 shows an alternative suction foot.
Figure 36:
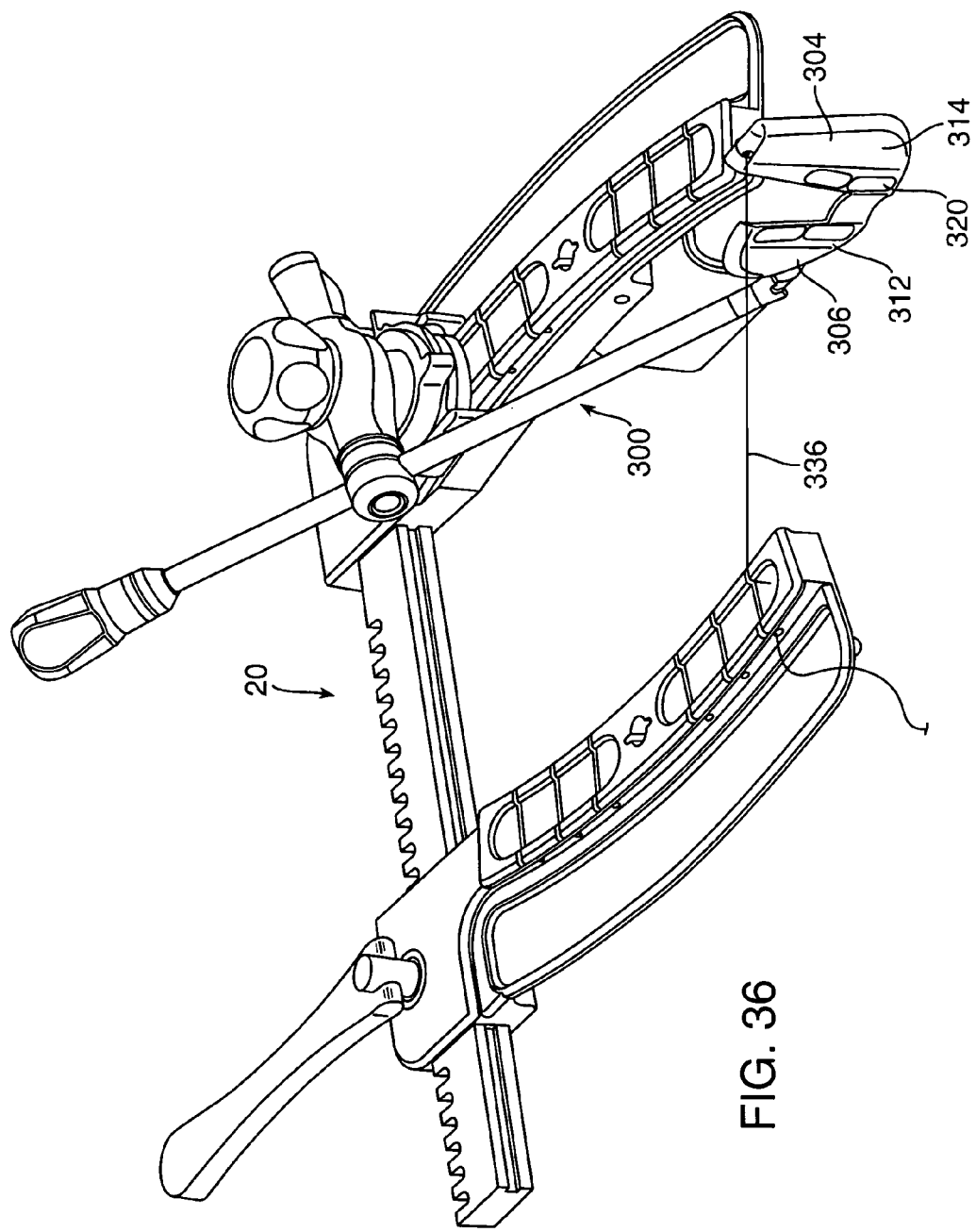
FIG. 36 shows another foot.
Figure 37:
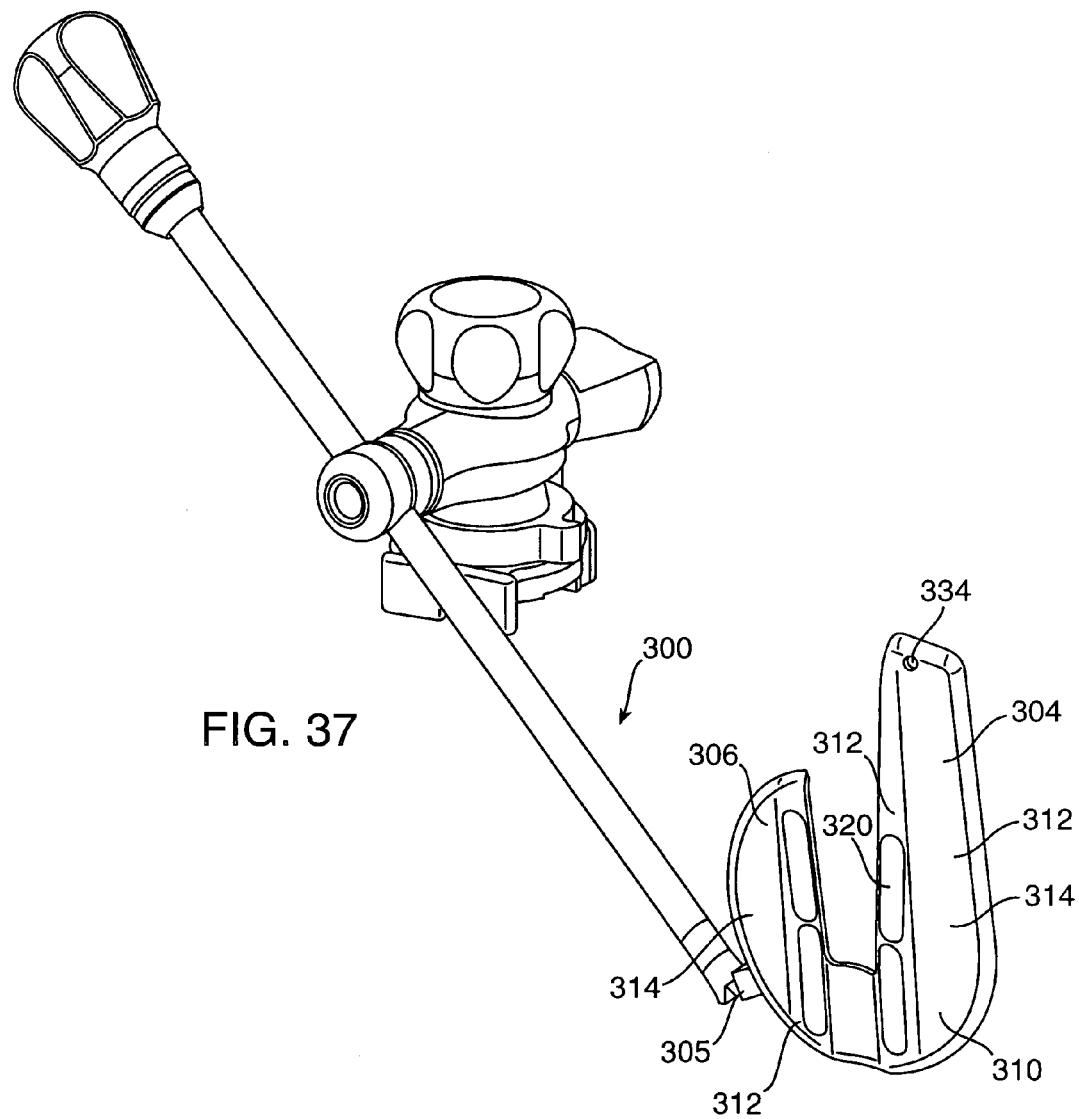
FIG. 37 shows the foot of FIG. 36.
Figure 40:
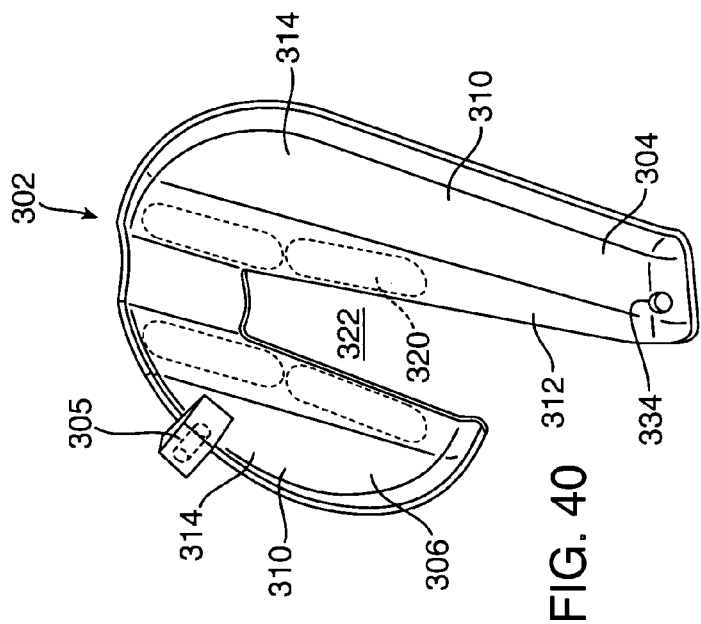
FIG. 40 is an isometric view of the foot of FIG. 36.
Figure 39:
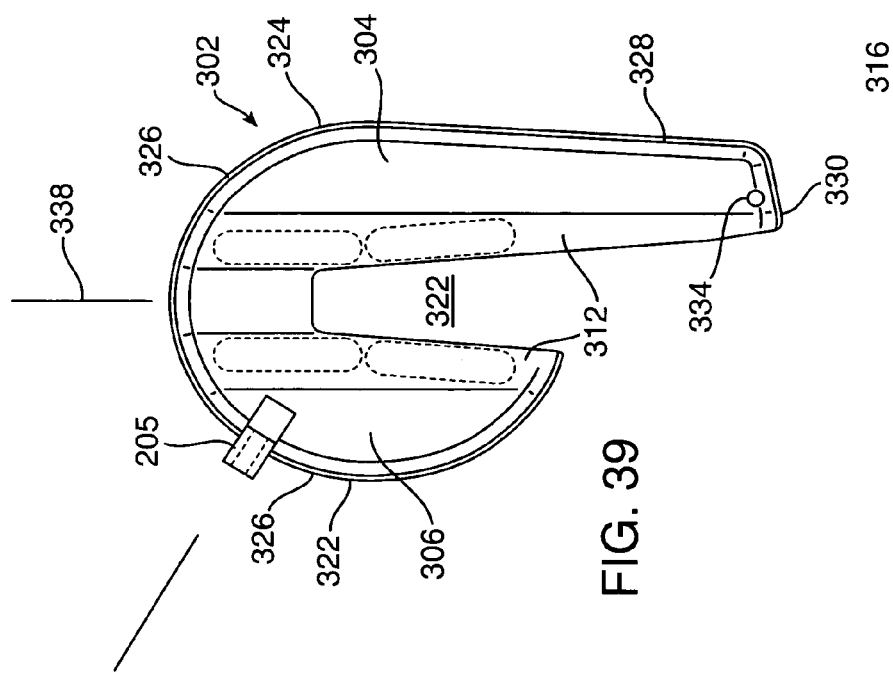
FIG. 39 is a top view of the foot of FIG. 36.
Figure 38:
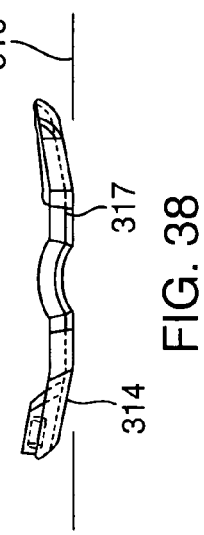
FIG. 38 is an end view of the foot of FIG. 36.

The foot 280 has a malleable frame 285 which is partially or completely covered by a body 286 which is preferably a polymer. The frame 285 is preferably made of 300 Series stainless steel and the polymer is preferably polycarbonate although any other suitable materials may be used. The foot 280 has flexible tips 287 formed by a hinge 290 at portions of the frame 285 (FIGS. 31 and 32). The hinges 290 are preferably formed by exposed portions of the frame 285 although the hinges 290 may also simply be at thinner portions of the body 286. Furthermore, the arms 288, 289 may be spread apart or moved together as shown in FIGS. 33 and 35. FIG. 35 shows the pin being mounted outside the bounds of the arms 288, 289 in the manner described above to provide the advantages described above.

In use, the foot 280 is positioned adjacent the target site and suction is activated to adhere the foot 280 to the heart. The foot 280 is then locked into position when the user has found an appropriate position for the foot 280 relative to the amount of mechanical force, if any, the user desires to apply to the heart. Alternatively, the foot 280 may be positioned at the desired site with only mechanical force with suction being activated afterward. Finally, although the foot 280 has the ability to provide suction stabilization, the foot 280 may also be used for simple mechanical stabilization as well.

The tips 287 may be used to retract and stabilize portions of the heart and other structures adjacent the target site. An advantage of the tips 287 is that they may provide the necessary displacement at the adjacent structures without changing the ability to stabilize the target site in the desired fashion. In this manner, adjacent structures can be retracted to improve access and/or exposure. In a specific use of the foot 280, the tips 287 may be displaced after the foot 280 has been positioned at the target site. This gives the user the ability to provide only the amount of retraction and/or added stabilization required. Alternatively, of course, the tips may be bent before the foot is stabilized with the user trying various different orientations until an optimal orientation is achieved. The tips 287 form a movable portion 292 of the foot 280. The movable portion 292 is preferably formed at the tips of the arms but may be positioned in any other suitable location on the foot 280 such as on the sides of the foot 280.

Although the hinges 290 do not contain the suction lumen 281 and the tips 287 do not have the suction recesses 282, the suction lumen 281 may extend to the tips 287 with recesses 282 provided in the tips 287 without departing from the scope of the invention. The tips 287 are preferably ski-tip, arrow, or V-shaped but may, of course, take any other shape. The tips 287 preferably extend at least 0.25 inch and more preferably at least 0.50 inch from the hinge 290 to the distal end. Finally, although the hinge 290 is preferably formed by an integral portion of the frame 285, the hinge may also be a mechanical connection.

Referring to FIGS. 36–40, another stabilizer 300 is shown. The stabilizer 300 may be fixed in position with any type of device without departing from the scope of the invention such as with the flexible arm 204 and retractor 20 described above. In the embodiment of FIGS. 36–40, the stabilizer is coupled to a rigid shaft or arm, however, the shaft or arm may be malleable, articulating or hinged.

The stabilizer 300 has a foot 302 having a first arm 304 and a second arm 306. The first arm 304 is shaped differently than the second arm 306, and is preferably larger than the second arm 306, which provides the advantages described below. The stabilizer 300 is particularly suited to stabilize the circumflex coronary artery in the manner described below but may, of course, be used for any other part of the heart. The first arm 304 not only stabilizes the coronary artery but also retracts another part of the heart, such as the apex, to improve visualization and/or access. The foot 302 may be made of any suitable material and is preferably made of injection molded plastic or stainless steel. The foot 302 may also be malleable so that the foot 302 may be shaped by the surgeon. The foot 302 has a connector 305 to releasably couple the foot to the arm or shaft.

The foot 302 has a bottom surface 310 is generally convex and is formed by central surfaces 312 and lateral surfaces 314. The lateral surfaces 314 taper upwardly away from the central surfaces 312. The lateral surfaces 314 are preferably flat and form an angle of 5–15 degrees, preferably about 9 degrees, with a plane 316 on which the central surfaces 312 lie. Although the bottom surface 310 is formed by generally flat surfaces, the lateral surfaces 314 may, of course, be curved.

The first and second arms 304, 306, and in particular the first arm 304, have relatively large bottom surfaces 310 to provide improved stabilization of the coronary artery and to retract other parts of the heart. The bottom surface 310 of the first arm 304 is preferably at least 30% larger and more preferably at least 50% larger than the bottom surface 310 of the second arm 306. Although the surface areas refer to the uninterrupted nature of the bottom surface, the foot 302 may have holes or openings while generally enclosing the surface areas described above.

The lateral surfaces 314 do provide some additional stabilization of the heart but, more importantly, the lateral surfaces 314 retract adjacent portions of the heart to provide improved access and/or visualization. An advantage of the bottom surface 310 is that the lateral surfaces 314 do not compress the heart as much as they would if they were not raised relative to the central surfaces 312. By curving, sloping and/or tapering the lateral surfaces 314 away from the contact surfaces 312, the lateral surfaces 314 compress and restrict the heart less than they otherwise would. Although the lateral surfaces 314 preferably taper away from the central surfaces 312, the lateral surfaces 314 may take any other shape, including planar or even concave, without departing from the scope of the invention.

Friction surfaces 320 which engage the heart lie within the central surfaces 312. The frictional surfaces 320 are preferably formed by etching although the friction surfaces 320 may be formed in any other suitable manner and may even be replaceable elements. The friction surfaces 320 protrude slightly below the central surfaces 312 but generally lie on the same plane 316 as the central surfaces 312. The friction surfaces 320 may also be positioned on both sides of the foot 302.

The second arm 306 has an outer edge 322 which is preferably curved but may take any other shape. The outer edge 322 has a radius of curvature of about 0.200 inch. The first arm 304 also has an outer edge 324 with a curved portion 326 having the same radius of curvature as the outer edge 322 of the second arm 306. The outer edge 322 of the second arm 306 has a relatively straight extension 328 extending to a distal end 330.

A slot 332 is formed between the first and second arms 304, 306. The slot 32 is preferably tapered toward the distal end 330. The slot 332 preferably forms an angle of 5–20 degrees and more preferably about 10 degrees. Although the slot 332 has straight sides, the slot 332 may also have a curved surface which tapers distally.

The foot 302 preferably has an eyelet 334, hook, slot or other suitable structure, which receives a filament 336 such as a suture or silastic. The filament 336 is tensioned to apply additional stabilizing force to the foot 302. The filament 306 is preferably coupled to the retractor 20 but may, of course, be attached to any other structure.

Figure 43:
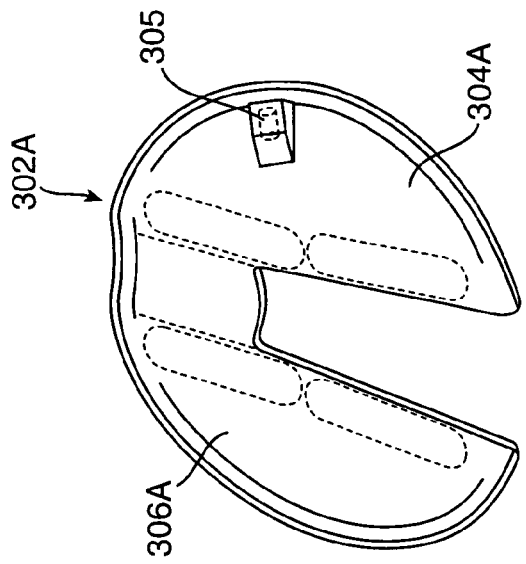
FIG. 43 is an isometric view of the foot of FIG. 41.
Figure 42:
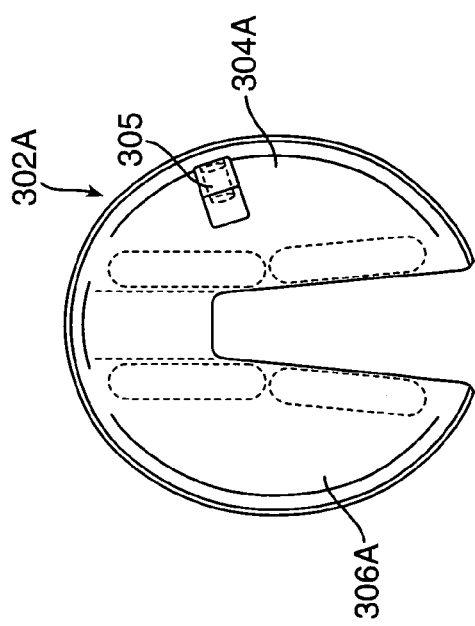
FIG. 42 is a top view of the foot of FIG. 41.
Figure 41:
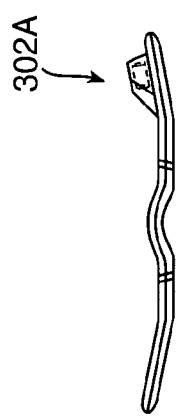
FIG. 41 is an end view of another foot.

Referring to FIGS. 41–43, another foot 302A is shown wherein the same or similar reference numbers refer to the same or similar structure. The first and second arms 304A, 306A of the foot 302A are essentially the same as the second foot 302 of the stabilizer 300 described above and the foot 302 provides many of the same advantages as the foot 302. The foot 302 has the connector 305 which connects to the shaft or arm. The connector 305 forms an angle of 50–90 degrees, more preferably 60–80 degrees and most preferably about 70 degrees with a central axis 338. The foot 302A is particularly useful for stabilizing distal branches of the right coronary artery.

The feet 302, 302A are preferably removably attached to the arm or shaft. An advantage of the present invention is that more than one foot 302, 302A may be used to perform multi-vessel coronary artery bypass. The feet 302, 302A have different shapes so that different vessels and different parts of the heart can be stabilized with the appropriate foot 302. As mentioned above in connection with FIGS. 27 and 28, the connectors 305 may be on opposite sides of the foot 302 to provide an appropriate arm for various parts of the heart.

Figure 11:
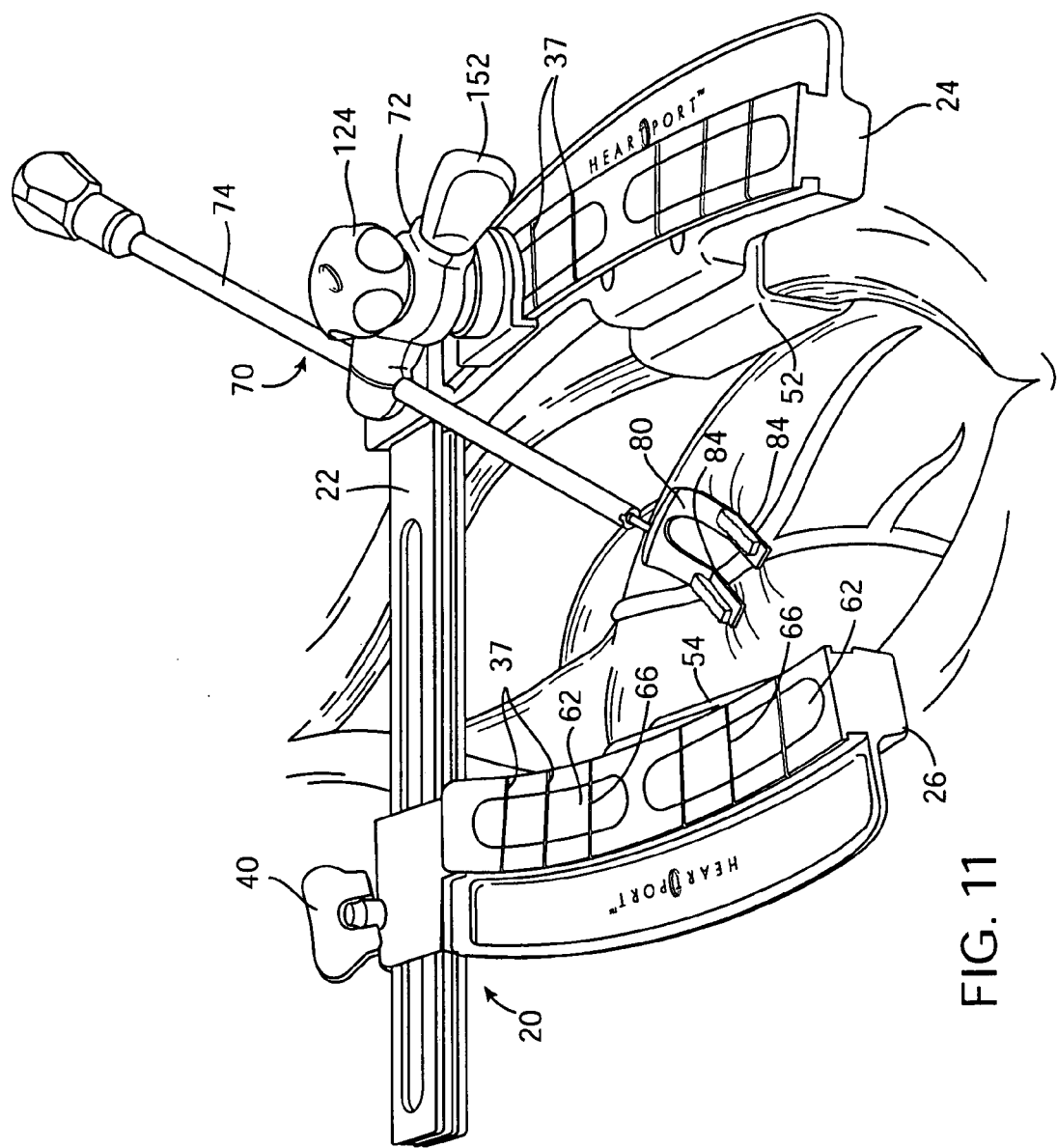
FIG. 11 is a perspective view of the system of FIG. 1 in position in an incision in a patient's chest.

In use, retractor 20 of the invention is placed in sternotomy incision as shown in FIG. 11. First and second blades 52, 54 of appropriate size and shape are attached to stationary arm 24 and movable arm 26. Movable arm 26 is positioned close to stationary arm 24 so that blades 52, 54 can be inserted into the incision. Key 40 is then turned to move movable arm 26 away from stationary arm 24, whereby by first and second blades 52, 54 retract the opposing tissue edges and widen the incision to expose the chest cavity. An incision is made in the pericardium (not shown in FIG. 11) and sutures are placed in the pericardial flaps. The sutures are drawn out of the chest and placed through channels 37 into slots 66 in suture stays 62, and tensioned until the pericardial flaps are drawn out of the way to expose the surgical site on the heart. The pericardial sutures may then be clamped in position in suture stays 62.

When it is time to perform the coronary anastomosis, mounting base 72 for stabilizer 70 is positioned along one of rails 28, 29 or on crossbeam 22 at the desired position, and lever 104 is actuated to lock mounting base 72 in position. Stabilizer 70 is then positioned so that foot 80 engages the epicardium near the anastomosis site. Usually, arms 84 are positioned on opposing sides of the target coronary artery aligned with the anastomosis site. Alternatively, one of arms 84 may be positioned so as to engage the coronary artery itself upstream of the anastomosis site to occlude the coronary artery to provide hemostasis during the anastomosis. Once positioned, stabilizer 70 is locked in position by tightening cap 124 and knob 152. Stabilizer 70 maintains relative stillness in the heart wall in the area of the anastomosis, while the heart continues to beat and the remainder of the heart wall contracts.

Figure 12A:
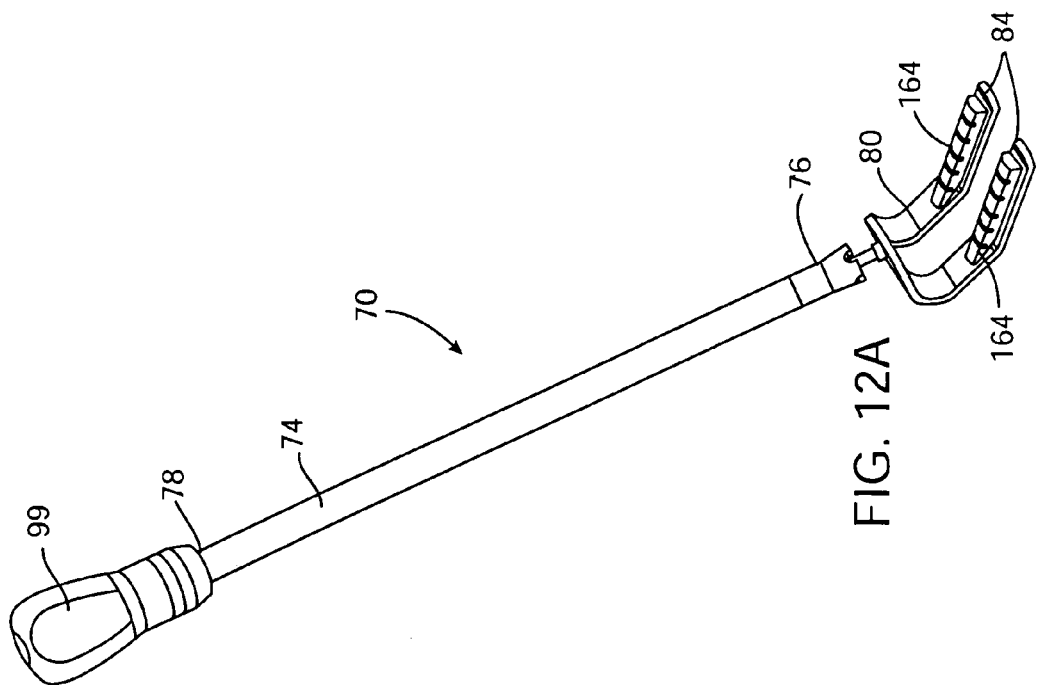
FIG. 12A is a perspective views of a further embodiment of a stabilizer according to the invention.
Figure 12B:
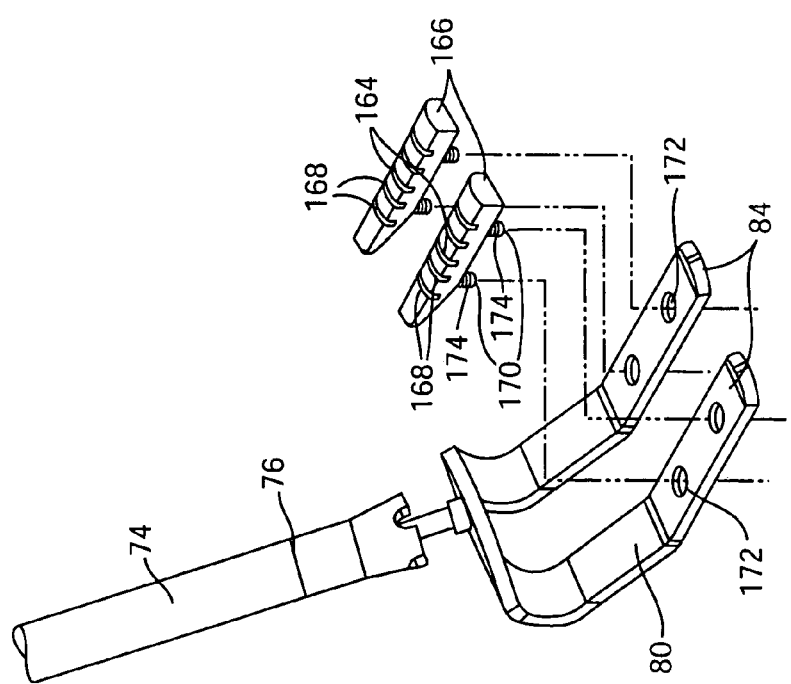
FIG. 12B is a perspective assembly view of a distal portion of the stabilizer of FIG. 12A.

FIGS. 12A–12B illustrate an additional embodiment of stabilizer 70 of the invention. In this embodiment, stabilizer 70 includes a pair of suture retainers 164 which may be mounted to foot 80. Preferably, retainers 164 are removable from foot 80 so that stabilizer 70 may be used with or without retainers 164 in place. Retainers 164 have a body 166 and a plurality of channels 168 configured to receive a suture or silastic used in the particular surgical procedure being performed. Channels 168 are dimensioned to frictionally engage the suture or silastic material with sufficient force to retain the material under tension, preferably having a width of about 0.010–0.030 in. and a depth of about 0.10–0.20 in, depending upon the type and size of suture or silastics utilized. In this way, sutures or silastics may be placed under the target coronary artery so as to form a sling on one or both sides of the anastomosis site, and the sutures or silastics may be tensioned to better expose the coronary artery relative to the surrounding myocardium, as well as to occlude the coronary artery for hemostasis. The sutures or silasatics may then be placed in channels 168 and are retained therein under tension during the procedure. In a preferred embodiment, retainers 164 have two pins 170 which extend from the bottom surfaces thereof and are received in holes 172 in foot 80. Pins 170 have flanges 174 which snap into holes 172 and retain pins 170 therein. Retainers 164 and pins 170 may be metal, rubber or plastic.

Figure 13:
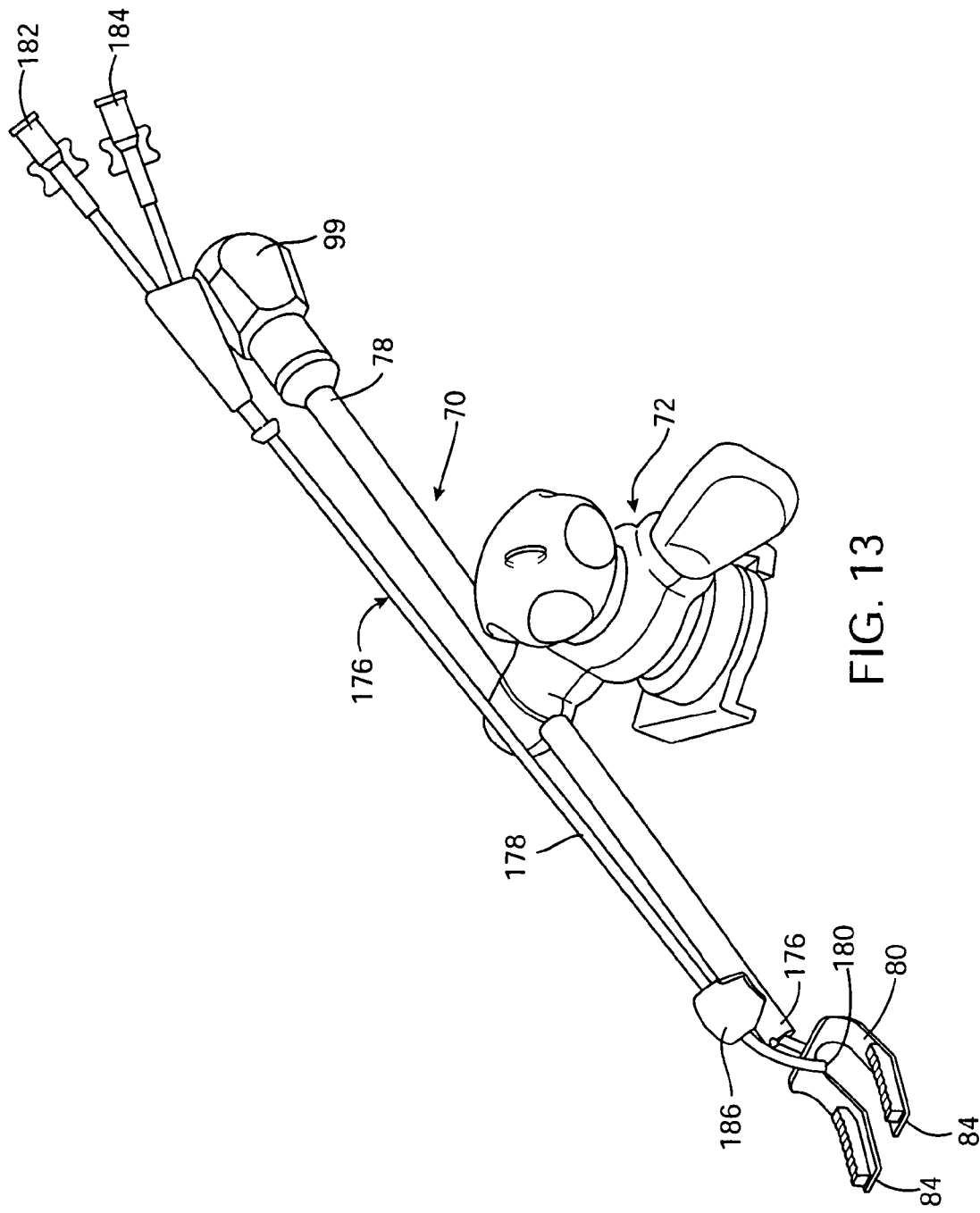
FIG. 13 is a perspective view of a stabilizer and blower according to the invention.

FIG. 13 illustrates an additional embodiment of stabilizer 70 of the invention. In this embodiment, a blower 176 is coupled to stabilizer 70 to allow for the delivery of a gas such as $CO_2$ to the surgical site. This helps to keep the site free of fluids and debris, as well as helps to inhibit the introduction of oxygen into the coronary arteriotomy. Blower 176 includes a shaft 178 having at least one inner lumen extending therethrough. Preferably, a second inner lumen is also provided. The inner lumens communicate with at least one opening at the distal end 180 of shaft 178, and with inlet ports 182, 184 at the proximal end of shaft 178. Inlet port 182 may be connected to a supply of gas such as $CO_2$, while inlet port 184 may be connected to a source of saline for irrigating or misting the surgical site, or to a source of suction for aspirating fluid and debris. Both inlet ports 182, 184 may be in communication with a single inner lumen in shaft 178, or each inlet port may be in communication with a separate inner lumen in the shaft. At least one clip 186 is attached to shaft 178 and is configured to be removably coupled to shaft 78 of stabilizer 70. Preferably, blower 176 is positionable such that its distal end 180 is disposed between arms 84 of foot 80 and close to the proximal end of the foot so as to deliver or suction fluids from the site without interfering with the anastomosis.

Figure 14A:
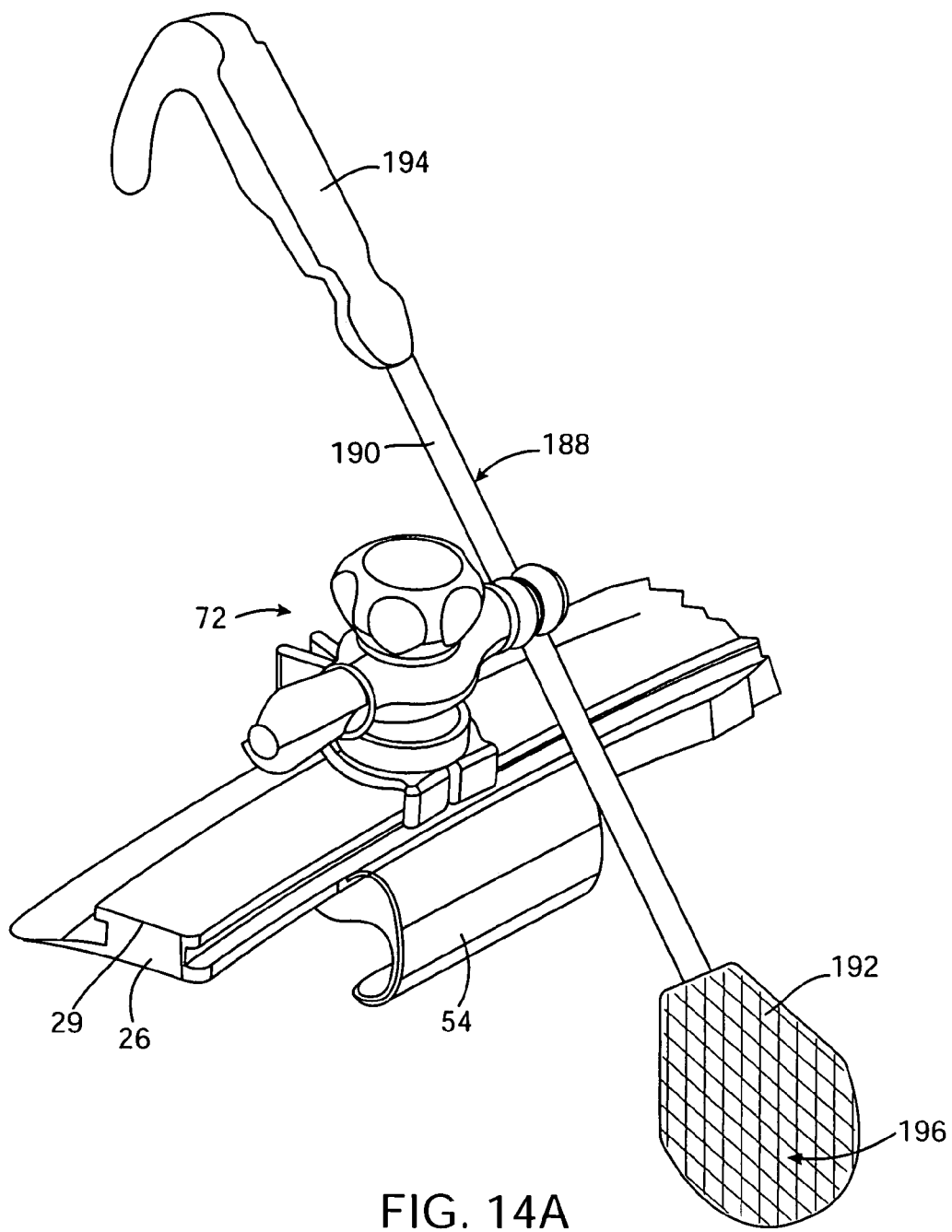
FIGS. 14A–C are perspective, top and side views, respectively, of a heart retractor according to the invention.
Figure 14B:
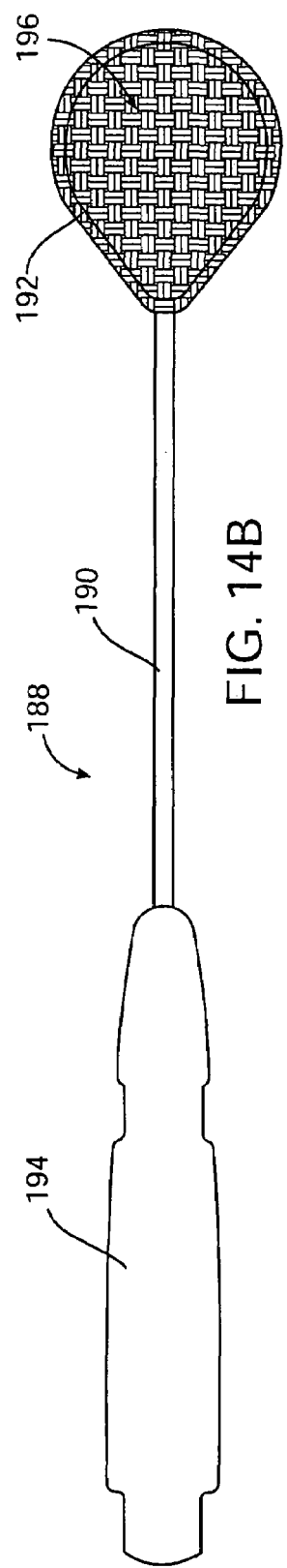
Figure 14C:
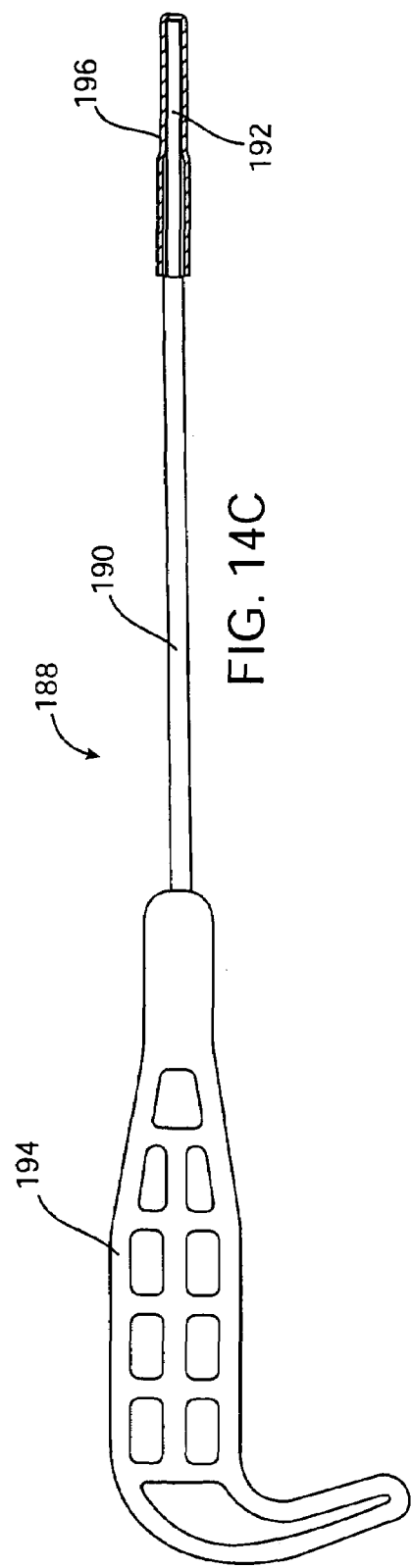

FIGS. 14A–14C illustrate a heart retractor which may be utilized with the system of the invention. Heart retractor 188 has a shaft 190 with a paddle 192 at its distal end and a handle 194 at its proximal end. Paddle 192 is covered with a soft, friction-enhancing and preferably absorbent material 196 such as adhesive-backed Dacron gauze. Paddle 192 is dimensioned to enable engagement with the outer wall of the heart and rolling, lifting or pushing the heart into a desired location during a surgical procedure, preferably having a width of about 1–3 inches and a length of about 2–4 inches across its face. Handle 194 is configured to be gripped by a surgeon's hand and is lightweight and compact, preferably being made of a lightweight plastic. Heart retractor 188 is preferably clamped onto rails 28, 29 or crossbeam 22 by means of mounting base 72 utilized with stabilizer 70, as described above. In this way, heart retractor 188 may be used to manipulate the heart into a desired position, and the heart retractor may be locked in place on retractor 20 to maintain the heart in position while an anastomosis or other procedure is performed. This facilitates the performance of anastomoses on the sides and back of the heart to enable multi-vessel coronary bypass procedures.

FIGS. 15A–B illustrate a vascular clamp holder that may be utilized with the system of the invention. Vascular clamp holder 200 includes a clip 202 configured to removably attach to a commercially-available vascular clamp 203 such as a Fogarty Clamp, as shown. Clip 202 has a slot 204 configured to receive a button 206 on the vascular clamp, and an axial channel 208 through which a shaft 209 of the vascular clamp may extend. Axial channel 208 has a side opening 210 through which shaft 209 may be placed in the channel, the side opening preferably having a width slightly smaller than shaft 209 so that the shaft is maintained in channel 208 once inserted therein. A malleable rod 212 extends from clip 202 to mount 214 and may be shaped in order to place clip 202 in a desired position. Mount 214 is configured to be attached to rails 28, 29 or crossbeam 22 on retractor 20, and may be constructed in a manner similar to that described above for mounting base 72. However, mount 214 need not have the same degree of positionability as mounting base 72, allowing both spherical joints to eliminated. Thus, mount 214 has a carriage 216 like carriage 90 described above, and is adapted for slidable engagement with rails 28, 29 or crossbeam 22. Carriage 216 has a living hinge 218 about which an outer portion 220 rotates relative to inner portion 222. A rotatable lever 224 has a cam 226 which engages a camming surface 228 on outer portion 220 to urge it against rails 28, 29 or crossbeam 22, thus locking mount 214 in place.

While the above is a complete description of the preferred embodiments of the invention, it will be appreciated that various equivalents, modifications, additions and substitutions may be made without departing from the scope thereof. Therefore, the above should not be taken as limiting the scope of the invention, which is defined by the following claims. For example, any foot described herein may be used with any arm or shaft described herein. Furthermore, the terms "shaft" and "arm" may be used interchangeably. Furthermore, the invention provides various independent aspects and is not limited to a single indispensible feature, advantage or aspect. Thus, each feature or aspect of the invention may be considered independent of the other features, advantages and aspects of the present invention.

What is claimed is:

1. Apparatus for stabilizing an epicardial surface of the heart, comprising:
   a shaft; and
   a foot coupled to the shaft, the foot having a first arm, a second arm, and a space between the first and second arms, the first and second arms each having a contact surface for engaging the heart, a proximal end, a distal end and a length defined between the proximal and distal ends and within a plane defined by the bottom surface of said foot, the length of the first arm being longer than the length of the second arm, and wherein the foot has a bottom surface, the bottom surface including the contact surface of the first and second arms, the contact surface generally lying in the plane, the bottom surface also having lateral surfaces that taper away from the plane.

2. The apparatus of claim 1, wherein:
   the first arm is at least 30% longer than the second arm.

3. An apparatus for stabilizing an epicardial surface of the heart comprising:
   a foot including a bottom surface having a contact surface for engaging the heart, a slot in which a vessel on the heart may be positioned, wherein at least a portion of the bottom surface is generally convex as viewed along a central axis defined by the slot, and the bottom surface has lateral surfaces which taper away from the contact surface.

4. The apparatus of claim 3, wherein:
   the lateral surfaces taper away within an angle of 2–15 degrees.

5. The apparatus of claim 3, comprising:
   a shaft;
   the foot has a first arm, said first arm having a proximal end and a distal end, and a second arm, said second arm having a proximal end and a distal end, said first and second arms each attached to said foot at their respective proximal ends;
   a space between said first and second arms, said space defining a slot, said slot defining a long axis of said foot; and
   a connector for detachably engaging the foot to the shaft, said connector located along a lateral side of said foot, and forming an axis which makes an angle with said long axis of said foot.

6. The apparatus of claim 5, wherein said angle is between about 50–90 degrees.

7. The apparatus of claim 6, wherein said angle is about 70 degrees.

8. A method of performing a coronary anastomosis on a heart of a patient comprising:
   providing a stabilizer having a foot that includes a bottom surface having a contact surface for engaging the heart, a slot in which a vessel on the heart may be positioned, and wherein at least a portion of the bottom surface is generally convex as viewed along a central axis defined by the slot, and the bottom surface has lateral surfaces that taper away from the contact surface;
   accessing a coronary artery on the patient's heart;
   placing the foot in engagement with the heart so that the coronary artery is positioned in the slot and the first arm retracting the apex of the heart; and
   performing an anastomosis on the coronary artery.

9. The method of claim 8, wherein:
   the placing step is carried out with the coronary artery being an artery selected from arteries in the group consisting of the circumflex and branches of the right coronary arteries.

10. A method of performing coronary anastomoses on a heart of a patient comprising:
    providing a stabilizer system having a shaft, a first foot and a second foot having a shape different than the first foot;
    coupling the first foot to the shaft;
    placing the first foot in engagement with the heart so as to stabilize the surface thereof;
    performing an anastomosis on a first coronary artery which is stabilized by the first foot;
    decoupling the first foot from the shaft;
    coupling the second foot to the shaft;
    placing the second foot in engagement with the heart so as to stabilize the surface thereof; and performing an anastomosis on the second coronary artery with the second foot stabilizing the second coronary artery.

11. An apparatus for stabilizing an epicardial surface of the heart, comprising:
   a foot having a first arm and a second arm, each of said first and second arms having a proximal end and a distal end, said first and second arms each attached to said foot at their respective proximal ends;
   said first and second arms each having at least one contact surface for engaging the heart;
   a space between said first and second arms, said space defining a slot, said slot defining a long axis of said foot;
   said first and second arms each having a lateral surface attached thereto, said lateral surface tapering away from said contact surface to be generally convex when viewed along said axis of said slot.

12. The apparatus according to claim 11, further comprising a length defined between the proximal ends of said first and second arms and the distal ends of said first and second arms, said length of the first arm being longer than the length of said second arm.

13. The apparatus according to claim 12, wherein the length of said first arm is at least 30% longer than said second arm.

* * * * *